US010123907B2

(12) United States Patent
Sigismondo et al.

(10) Patent No.: US 10,123,907 B2
(45) Date of Patent: Nov. 13, 2018

(54) MUD VISOR FOR ROLL-OFF FILM SYSTEM

(71) Applicant: 100% SPEEDLAB, LLC, San Diego, CA (US)

(72) Inventors: Kevin Michael Sigismondo, San Diego, CA (US); Marc Guy Blanchard, San Diego, CA (US); Ludovic Francis Boinnard, San Diego, CA (US)

(73) Assignee: 100% SPEEDLAB, LLC, San Diego, CA (US)

( * ) Notice: Subject to any disclaimer, the term of this patent is extended or adjusted under 35 U.S.C. 154(b) by 202 days.

(21) Appl. No.: 14/701,434

(22) Filed: Apr. 30, 2015

(65) Prior Publication Data
US 2015/0328050 A1 Nov. 19, 2015

Related U.S. Application Data

(60) Provisional application No. 62/059,065, filed on Oct. 2, 2014, provisional application No. 61/994,665, filed on May 16, 2014.

(51) Int. Cl.
*A61F 9/00* (2006.01)
*A61F 9/02* (2006.01)

(52) U.S. Cl.
CPC .............. *A61F 9/025* (2013.01); *A61F 9/022* (2013.01)

(58) Field of Classification Search
CPC ................................. A61F 9/025; A61F 9/022
USPC ............................................... D16/311; 1/311
See application file for complete search history.

(56) References Cited

U.S. PATENT DOCUMENTS

| 3,945,044 A | * | 3/1976 | McGee | ................... | A61F 9/025 2/434 |
| 4,428,081 A | | 1/1984 | Smith | | |
| 4,748,697 A | * | 6/1988 | Hodnett | ................... | A61F 9/025 2/438 |
| 4,755,040 A | * | 7/1988 | Haslbeck | ............. | A63B 33/002 2/428 |
| 5,163,185 A | * | 11/1992 | Hodnett | ............... | A62B 18/082 2/422 |
| 5,913,416 A | * | 6/1999 | Rothan | ................... | A45C 11/04 2/13 |
| 5,966,745 A | * | 10/1999 | Schwartz | ................. | A42B 1/12 2/428 |

(Continued)

FOREIGN PATENT DOCUMENTS

| GB | 2378412 | 2/2003 |
| GB | 2495984 | 5/2013 |

*Primary Examiner* — Khaled Annis
(74) *Attorney, Agent, or Firm* — Haynes and Boone, LLP

(57) ABSTRACT

A mud visor formed by a substantially transparent sheet is attached to a goggle lens. The mud visor may be attached to the goggle lens using a substantially transparent adhesive or adhesive tape. Thus, the mud visor may provide clear and improved field of view for the user. Further, the mud visor may be configured to cover and guide a top portion of a roll-off film as the roll-off film is conveyed across the goggle lens. A top portion of the mud visor may be inserted into the lens groove of a goggle frame along with the goggle lens when the goggle lens is attached to the goggle frame. The mud visor also may stretch across the goggle lens and overlap with film canisters at both sides to provide a seamless coverage to prevent mud from entering behind the mud visor or the roll-off film.

20 Claims, 32 Drawing Sheets

(56) References Cited

U.S. PATENT DOCUMENTS

| | | | |
|---|---|---|---|
| 6,206,521 B1* | 3/2001 | Kindschuh | G02B 3/08 |
| | | | 351/159.58 |
| 6,415,452 B1* | 7/2002 | Watanabe | A61F 9/025 |
| | | | 2/438 |
| 6,416,177 B1 | 7/2002 | Gibson | |
| 7,866,812 B1* | 1/2011 | Tullis | G02C 9/04 |
| | | | 2/441 |
| 8,356,895 B2* | 1/2013 | Jackson | 351/159.01 |
| 2001/0029623 A1* | 10/2001 | Tsubooka | A61F 9/028 |
| | | | 2/436 |
| 2002/0166158 A1* | 11/2002 | Chiang | A63B 33/002 |
| | | | 2/428 |
| 2009/0119823 A1* | 5/2009 | Lee | B63C 11/12 |
| | | | 2/426 |
| 2009/0229044 A1* | 9/2009 | Gill | A42B 3/26 |
| | | | 2/434 |
| 2010/0033671 A1* | 2/2010 | Campo | A63B 33/002 |
| | | | 351/43 |
| 2012/0023647 A1 | 2/2012 | Park | |
| 2013/0104299 A1* | 5/2013 | Chen | A61F 9/029 |
| | | | 2/431 |
| 2014/0157496 A1* | 6/2014 | Ginther | A61F 9/025 |
| | | | 2/439 |

* cited by examiner

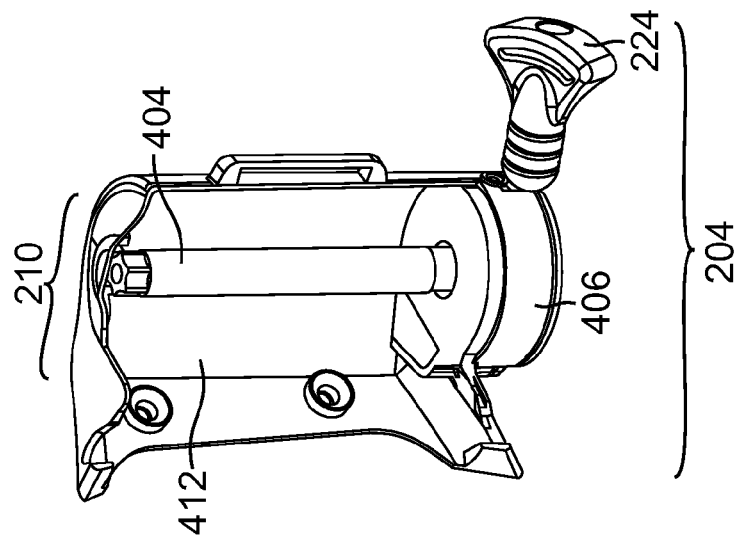
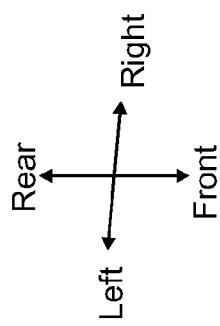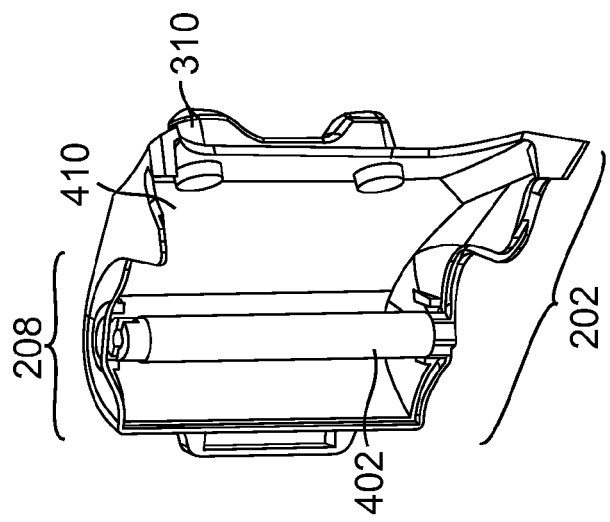
FIG. 4

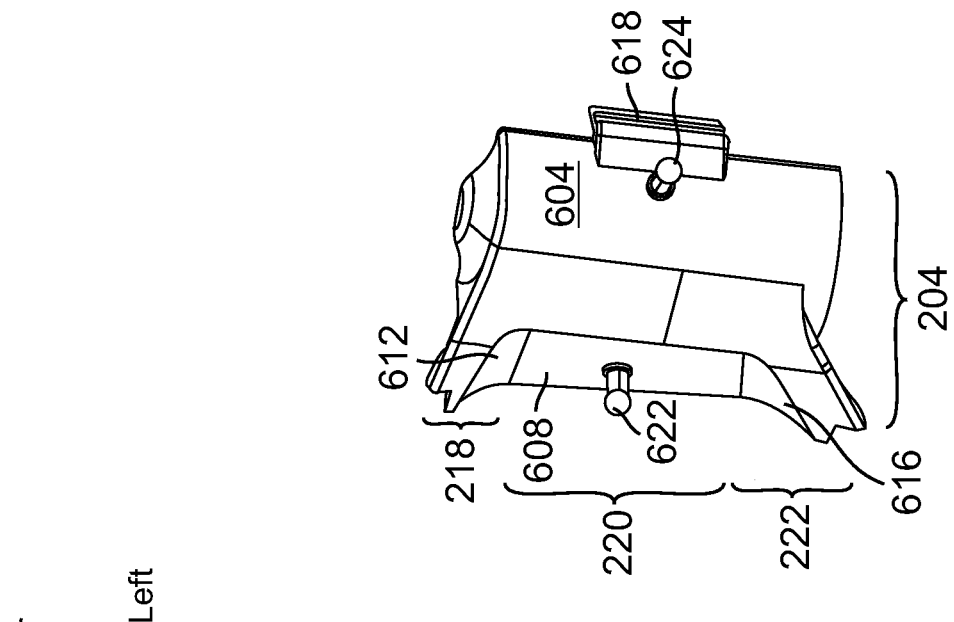
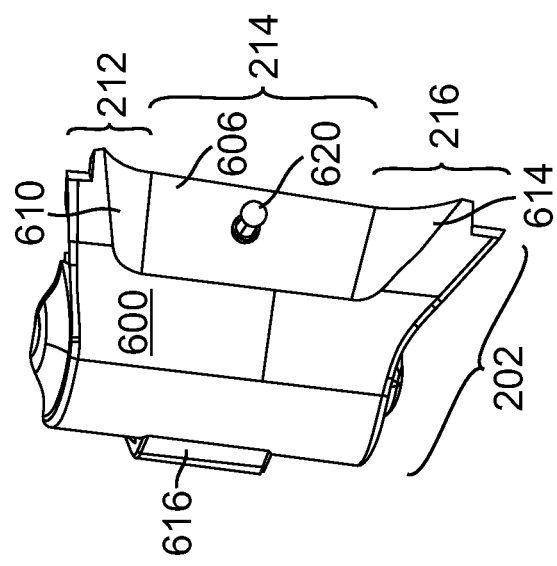
FIG. 6

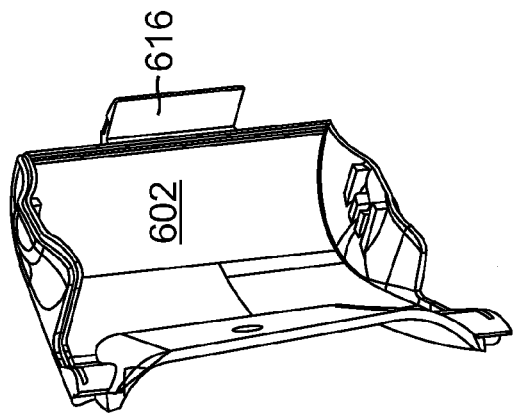
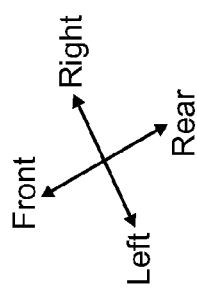
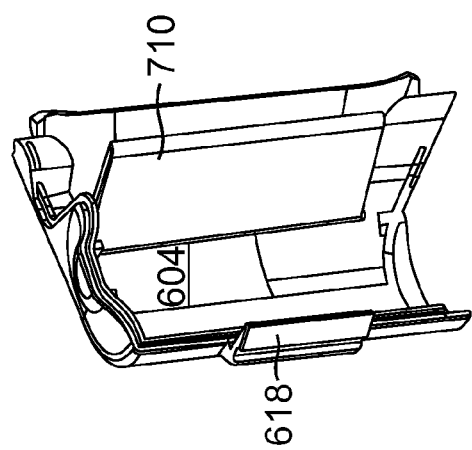
FIG. 7

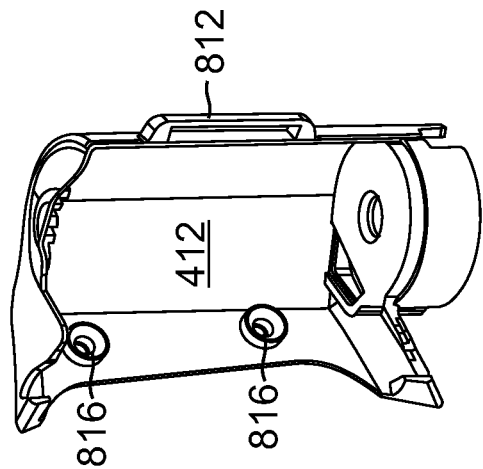
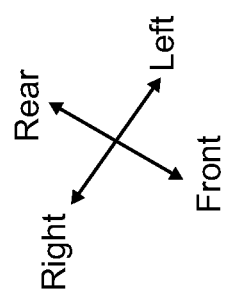
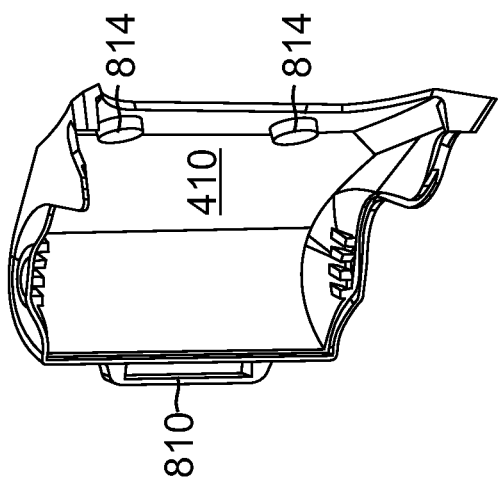
FIG. 8

MUD VISOR FOR ROLL-OFF FILM SYSTEM

CROSS-REFERENCE TO RELATED APPLICATIONS

This patent application claims the benefit of U.S. Provisional Patent Application No. 61/994,665, filed May 16, 2014 and entitled "Roll-Off Film System" and U.S. Provisional Patent Application No. 62/059,065, filed Oct. 2, 2014 and entitled "Mud Visor for Roll-Off Film System" which are hereby incorporated by reference in their entirety.

TECHNICAL FIELD

One or more embodiments relate generally to roll-off film systems and, more particularly, to the use of such film systems with sport goggles.

BACKGROUND

Sport goggles are worn by users for various sports or activities, such as motorsports, powersports, snowsports, watersports, biking, or the like, to protect users' eyes. A sport goggle may be installed with a roll-off film system to preserve a field of view on the lens of the sport goggle. In particular, the roll-off film system may stretch a section of a clear film across the lens of the sport goggle. When the section of the clear film is filled with dirt or debris from the sport activity, the roll-off film system may convey the used section of the clear film off the lens and a new section of the film may be conveyed onto the lens to provide a clear field of view for the user.

Nevertheless, dirt or mud still may enter through an interface between the roll-off film system and the lens of the goggle. This may reduce the field of view on the lens which may render the roll-off film system ineffective. As such, there is a need for an improved implementation that may address one or more of these shortcomings.

SUMMARY

Mud visors for roll-off film systems and methods are provided in accordance with one or more embodiments that may be installed on goggle lenses to provide improved field of vision for users. In an embodiment, a mud visor formed by a substantially transparent sheet is attached to the goggle lens. The mud visor may be attached to the goggle lens using a substantially transparent material. Thus, the mud visor may provide clear and improved field of view for the user. Further, the mud visor may be configured to cover and guide a top portion of the roll-off film as the roll-off film is conveyed across the goggle lens. A top portion of the mud visor may be inserted into the lens groove of the goggle frame along with the goggle lens when the goggle lens is attached to the goggle frame. The mud visor also may stretch across the goggle lens and overlap with the film canisters at both sides to provide a seamless coverage to prevent mud from entering behind the mud visor or the roll-off film.

In an embodiment, film canisters of the roll-off film systems may include contact portions configured to seamlessly contact the goggle frame or the adaptor to the goggle frame. Further, the film canisters may include blade sections configured to remove mud or dirt from a used section of clear film when the used section is conveyed into the film canister to prevent excess mud or dirt from entering the film canister. The blade sections may also be configured to slant away from the field of view on the lens to allow the mud or dirt to fall away from the field of view on the lens to provide better field of view for the user.

In accordance with an embodiment, a roll-off film system may include a film dispensing canister configured to store and dispense a film and a film receiving canister configured to receive the film dispensed from the film dispensing canister. The film receiving canister may include a blade portion configured to cover the film when the film is conveyed into the film receiving canister.

In accordance with an embodiment, the film receiving canister is attached to a lens and a surface of the blade portion forms an obtuse angle with a surface of the lens. In accordance with an embodiment, the film receiving canister further may include an upper wing portion and a lower wing portion with the blade portion disposed between the upper and the lower wing portions. The upper wing portion and the lower wing portion may extend further upstream in a film conveying direction of the film than the blade portion.

In accordance with an embodiment, an edge of the blade portion is configured to slide on the film when the film is conveyed into the film receiving canister. An upper portion of the edge protrudes further upstream in a film conveying direction than a lower portion of the edge.

In accordance with an embodiment, a goggle assembly may include a lens, a lens frame configured to receive the lens, and a roll-off film system attached to the lens. The roll-off film system may include a film dispensing canister configured to store and dispense a film across a front surface of the lens in a film conveying direction and a film receiving canister configured to receive the film dispensed across the front surface of the lens from the film dispensing canister. The film receiving canister may include a blade portion configured to cover the film when the film is conveyed into the film receiving canister. In an embodiment, the lens frame is disposed in a front portion of a goggle frame. In another embodiment, the lens frame is an adaptor attachable to a goggle frame.

In accordance with an embodiment, a method includes conveying a film from a film dispensing canister across a front surface of a lens to a film receiving canister, and collecting debris on the film at a blade portion of the film receiving canister before the film is conveyed into the film receiving canister. The method also includes directing the debris collected on the blade portion away from a field of view of the lens by a slanting edge of the blade portion.

The scope of the invention is defined by the claims, which are incorporated into this Summary by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 4 shows an exposed view of the roll-off film system of FIG. 1, in accordance with an embodiment.

FIG. 6 shows a perspective front view of front casings, in accordance with an embodiment.

FIG. 7 shows a perspective rear view of the front casings of FIG. 6, in accordance with an embodiment.

FIG. 8 shows a perspective front view of rear casings, in accordance with an embodiment.

Embodiments of the invention and their advantages are best understood by referring to the detailed description that follows. It should be appreciated that like reference numerals are used to identify like elements illustrated in one or more of the Figures.

DETAILED DESCRIPTION

Figure 1:
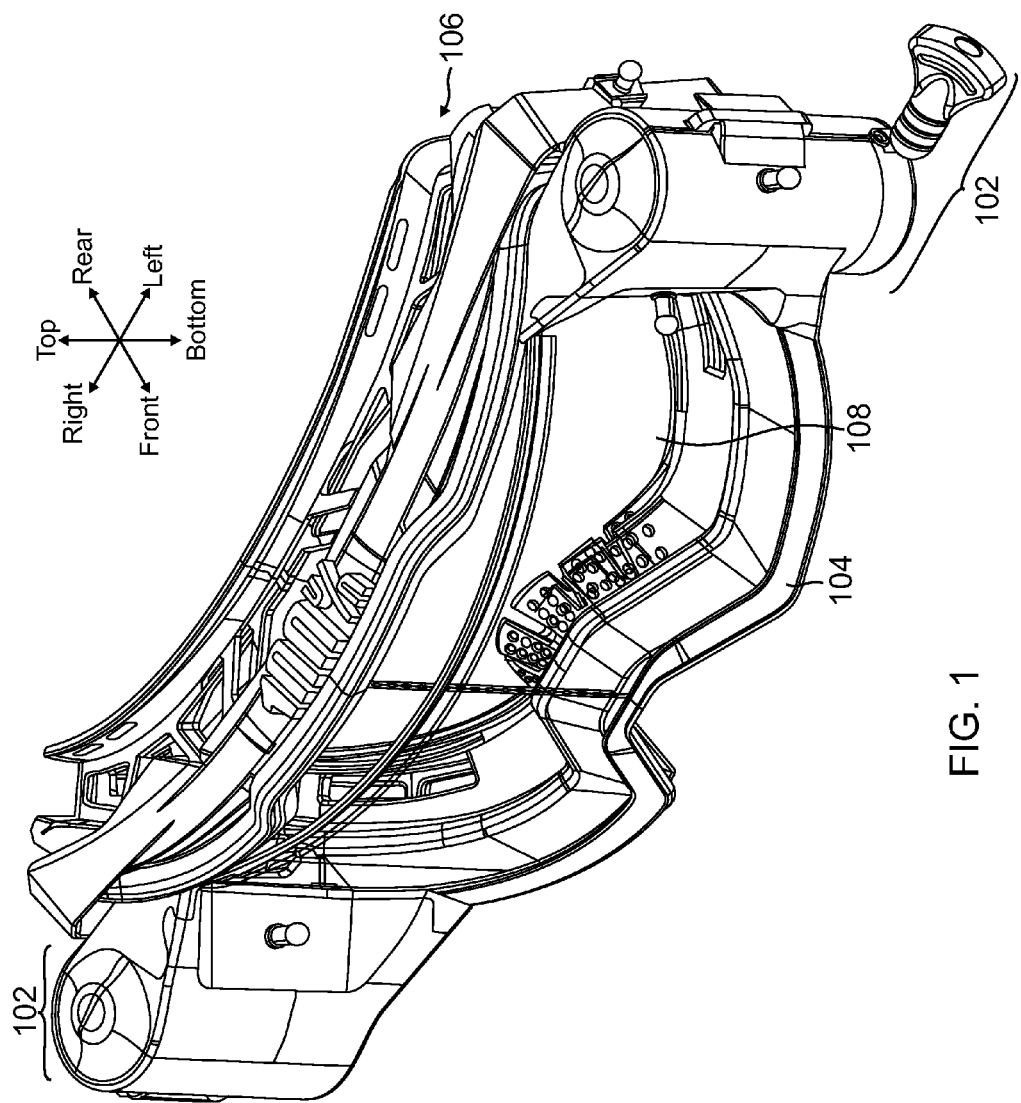
FIG. 1 shows a perspective front view of a roll-off film system installed on a goggle, in accordance with an embodiment.

A roll-off film system configured to attach to a goggle frame or an adaptor to a goggle frame is disclosed in accordance with various embodiments. The roll-off film system may include a film dispensing canister configured to dispense a film across a goggle lens to a film receiving canister. In particular, the film receiving canister may include a blade portion configured to collect dirt or debris landed on the film before the film is conveyed into the film receiving canister. The blade portion may have an edge sloping away from a field of view of the goggle lens with respect to a film conveying direction, such that the dirt or debris collected on the blade section may be guided away from the field of view of the goggle lens to improve a user's view through the goggle lens. The film dispensing canister also may include a similar blade portion.

According to an embodiment, each of the film dispending canister and the film receiving canister may include an upper wing portion configured to extend over a mud flap of the goggle lens to prevent dirt or debris from entering an interface between the canister and the film. Each of the film dispending canister and the film receiving canister also may include a lower wing section configured to extend under a lower portion of the section of the film stretched across the goggle lens. Thus, the upper wing sections, the lower wing sections, and the blade portions of the film dispensing and receiving canisters, and the mud flap on the goggle lens effectively form a continuously barrier to prevent dirt or debris from entering between the film and the goggle lens.

In an embodiment, a front surface of the blade portion of the film receiving canister may form an obtuse angle with the goggle lens, such that the blade section may act as a shovel to pick up the dirt or debris landed on the film when the film is conveyed into the film receiving canister. Thus, the blade section may prevent or reduce the amount of dirt or debris on the film from entering the film receiving canister with the film.

In an embodiment, a mud visor formed by a substantially transparent sheet is attached to the goggle lens. The mud visor may be attached to the goggle lens using a substantially transparent adhesive or adhesive tape. In particular, the adhesive or the adhesive tape is applied along a perimeter area of the mud visor, leaving the center area of the mud visor free from adhesives. In another embodiment, the substantially transparent adhesive, such as optical adhesive, may also be applied to the center area of the mud visor. Thus, the mud visor may provide clear and improved field of view for the user. Further, the mud visor may be configured to cover a top portion of the roll-off film conveyed across the goggle lens. A top portion of the mud visor may be inserted into the lens groove of the goggle frame along with the goggle lens when the goggle lens is attached to the goggle frame. Thus, the mud visor may prevent mud from entering behind the mud visor from the top side. The mud visor also may stretch across the goggle lens and overlap with the film canisters at both sides to provide a seamless coverage to prevent mud from entering behind the roll-off film.

FIG. 1 shows a perspective front view of a roll-off film system installed on a goggle, in accordance with an embodiment. As shown in FIG. 1, a goggle frame 106 may be installed with a roll-off film system 102. In particular, the roll-off film system 102 may be installed to the goggle frame 106 via an adaptor 104. The adaptor 104 may adapt the goggle frame 106 to use different goggle lenses and/or accessories. For example, the adaptor 104 may adapt the goggle frame 106 to use lenses of different sizes, shapes, curvatures, and the like. The adaptor 104 also may adapt the goggle frame 106 to use roll-off film systems of different film sizes.

The roll-off film system 102 may be attached to the lens 108, which is installed in the adaptor 104. The adaptor 104 may be attached to the goggle frame 106. In some embodiments, the lens 108 may be installed directly to the goggle frame 106, without the adaptor 104. Thus, the roll-off film system 102 may be installed on the goggle frame 106 without using the adaptor 104. The roll-off film system 102 may stretch a section of a film on the lens 108. When the section of the film becomes filled with dirt or debris, the used section of the film may be conveyed off the lens 108 and a new section of the film may replace the used section of the film to provide the user with clear field of view on the lens 108.

Figure 2:
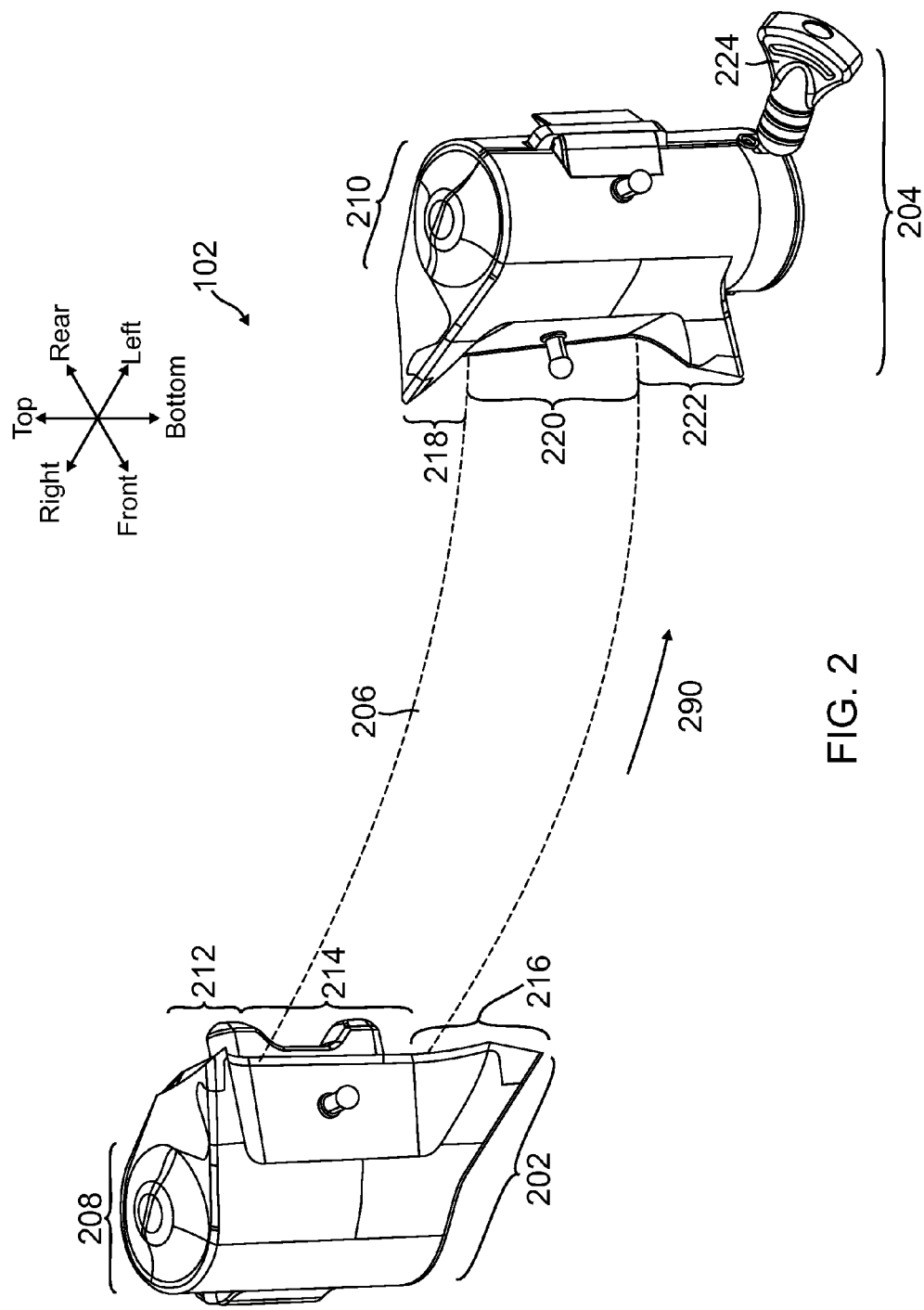
FIG. 2 shows a perspective front view of the roll-off film system of FIG. 1, in accordance with an embodiment.
Figure 3:
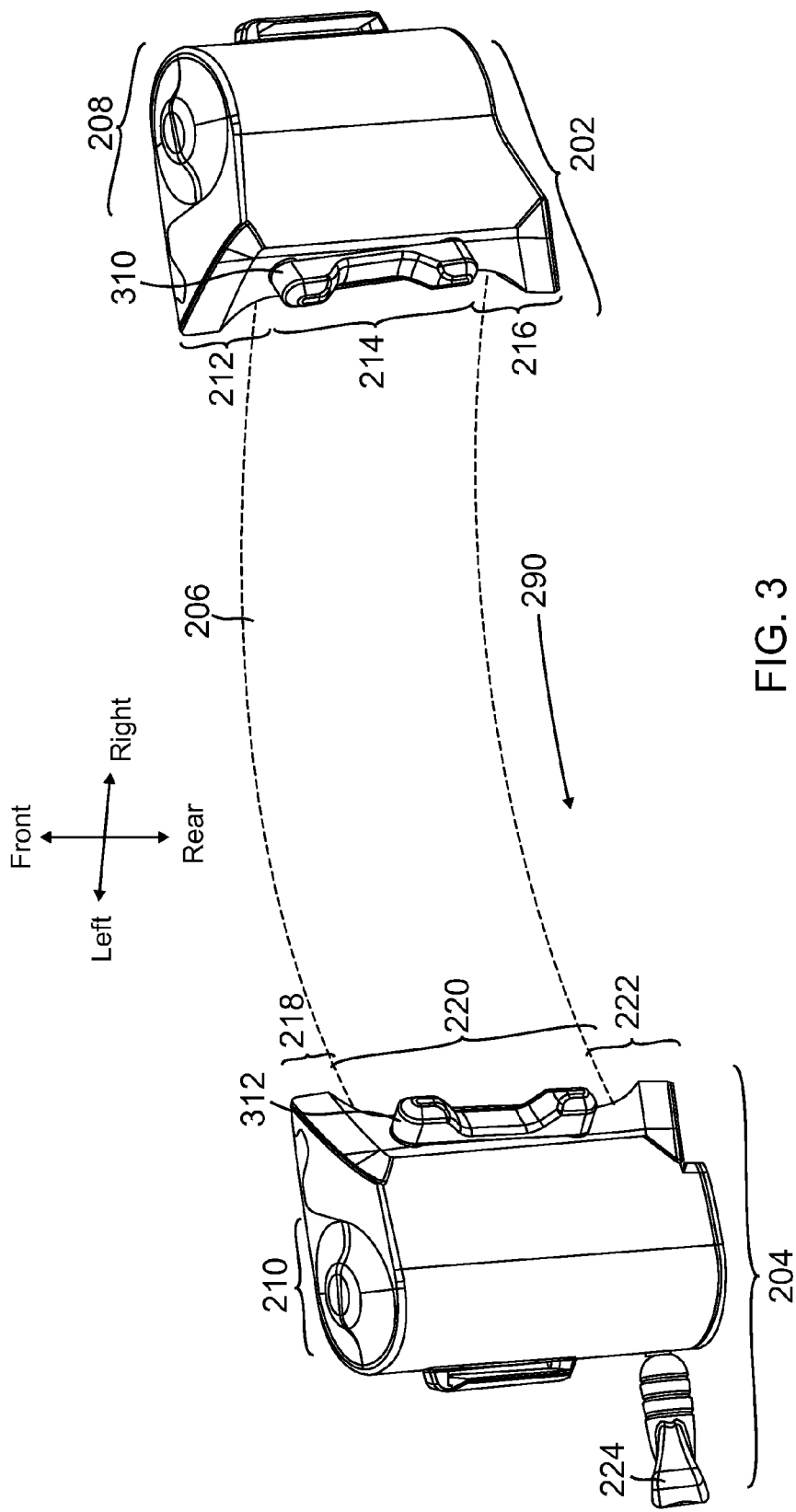
FIG. 3 shows a perspective rear view of the roll-off film system of FIG. 1, in accordance with an embodiment.

FIGS. 2 and 3 show perspective front and rear views of the roll-off film system of FIG. 1, in accordance with an embodiment. As shown in FIGS. 2 and 3, the roll-off film system 102 may include a film dispensing canister 202 and a film receiving canister 204. The film dispensing canister 202 may dispense a section of a film 206 across the lens 108 toward the film receiving canister 204. The film receiving canister 204 may receive the film 206 from the film dispensing canister 202. The film receiving canister 204 may include a pull cord handle 224, which is attached to an end of a string configured to drive a conveyance of the film 206 from the film dispensing canister 202 to the film receiving canister 204 in a film conveying direction 290. For example, when the section of the film 206 resting on the lens 108 becomes filled with dirt or debris, a user may pull the pull cord handle 224 to roll the used section of the film 206 into the film receiving canister 204 and to convey a new section of the film 206 onto the lens 108 to provide clear field of view on the lens 108.

The film dispensing canister 202 may include a film storage portion 208 within which the film 206 may be stored. The film dispensing canister 202 also may include an upper wing portion 212, a lower wing portion 216, and a blade portion 214 disposed between the upper wing portion 212 and the lower wing portion 216. The upper wing portion 212 and the lower wing portion 216 may protrude further downstream in the film conveying direction 290 than the blade portion 214. The film 206 may exit the film dispensing canister 202 through an opening at the blade portion 214.

The film receiving canister 204 may include a film storage portion 210 within which the film 206 received from the film dispensing canister 202 may be stored. The film receiving canister 204 also may include an upper wing portion 218, a lower wing portion 222 and, a blade portion 220 disposed between the upper wing portion 218 and the lower wing portion 222. The upper wing portion 218 and the lower wing portion 222 may protrude further upstream in the film conveying direction 290 than the blade portion 220. The film 206 may be conveyed into the film receiving canister 204 through an opening at the blade portion 220. As shown in FIG. 3, the film dispensing canister 202 may include a lens attachment mechanism 310 configured to attach the film dispensing canister 202 to the lens 108. Similarly, the film receiving canister 204 may include a lens attachment mechanism 312 configured to attach the film receiving canister 204 to the lens 108.

FIG. 4 shows an exposed view of the roll-off film system of FIG. 1, in accordance with an embodiment. The film dispensing canister 202 may include a film dispensing axle 402 disposed in the film storage portion 208. Unused sections of the film 206 may be wound around the film dispensing axle 402 into a roll. The film dispensing axle 402 may rotate to unwind particular sections of the film 206 as the particular sections of the film 206 are dispensed from the film dispensing canister 202. The film receiving canister 204 may include a film receiving axle 404 disposed in the film storage portion 210. Used sections of the film 206 may be wound around the film receiving axle 404 into a roll. The film receiving axle 404 may be driven by a pull cord to rotate and to wind the film 206 into the film receiving canister 204. A pull cord housing 406 may be disposed under the film receiving axle 404.

Figure 5:
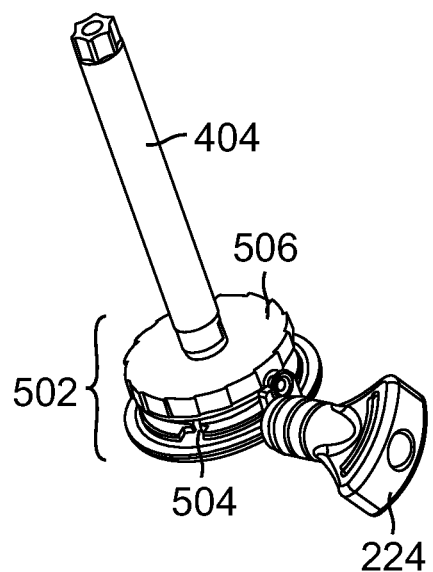
FIG. 5 shows a perspective view a ratchet mechanism, in accordance with an embodiment.

As shown in FIG. 5, a ratchet mechanism assembly 502 may be provided within the pull cord housing 406. The ratchet mechanism assembly 502 may include a ratchet 506 configured to transfer a pull force from a pull cord to the film receiving axle 402. A pull cord (not shown) connected to the pull cord handle 224 may be wound and stored under the ratchet 506 in the pull cord housing 406. When the user 224 pulls on the pull cord handle 224, the pull cord is unwound which may cause the ratchet 506 and the film receiving axle 404 to rotate. As the film receiving axle 404 rotates, additional sections of the film 206 may be wound onto the film receiving axle 404. This may cause a conveying motion along the film 206 which pulls a new section of the film 206 from the film dispensing canister 202 onto the lens 108. The ratchet mechanism assembly 502 may include a pull cord retracting mechanism (not shown) configured to automatically rewind the cord into the pull cord housing 406 after the cord is pulled. Thus, the cord may be ready to be pulled for conveying the next section of the film 206 onto the lens 108.

The film dispensing canister 202 may be formed by a front casing 602, as shown in FIG. 6, coupled to a rear casing 410, as shown in FIG. 4. The front casing 602 and the rear casing 410 may form a cavity for storing unused sections of the film 206. Similarly, the film receiving canister 204 may be formed by a front casing 604, as shown in FIG. 6, coupled to a rear casing 412, as shown in FIG. 4. The front casing 604 and the rear casing 412 may form a cavity for storing used sections of the film 206. The casings 602, 410, 604, and 412 may be formed with certain plastic resin, such as polycarbonate. In other embodiments, the casings may be formed with metal, synthetic material, bio-material, or the like. The casings may be formed by injection molding. In other embodiments, the casings may be formed by three-dimensional (3D) printing.

FIGS. 6 and 7 show perspective front and rear views of the front casings, in accordance with an embodiment. As shown in FIG. 6, the front casing 602 of the film dispensing canister 202 may include a coupling mechanism 616 configured to couple the front casing 602 to the rear casing 410. Similarly, the front casing 604 of the film receiving canister 204 may include a coupling mechanism 618 configured to fix the front casing 604 to the rear casing 412. Coupling mechanisms 616 and 618 each may include a deformable hook.

The upper wing portion 212 of the front casing 602 may include a triangular shaped surface 610. The blade portion 214 of the front casing 602 may include a sloping surface 606. The lower wing portion 216 of the front casing 602 may include a triangular shaped surface 614. The triangular shaped surface 610 may curve from facing down at a top portion thereof to facing a horizontal direction at a lower portion thereof. The triangular shaped surface 614 may curve from facing the horizontal direction at a top portion thereof to facing up at a lower portion thereof. The triangular shaped surface 610, the sloping surface 606, and the triangular shaped surface 614 may form a continuous, broad U-shaped surface. A tear-off pin 620 may be disposed on the sloping surface 606 at which a user may pull to separate the front casing 602 from the rear casing 410.

The upper wing portion 218 of the front casing 604 may include a triangular shaped surface 612. The blade portion 220 of the front casing 604 may include a sloping surface 608. The lower wing portion 222 of the front casing 604 may include a triangular shaped surface 616. The triangular shaped surface 612 may curve from facing down at a top portion thereof to facing a horizontal direction at a lower portion thereof. The triangular shaped surface 616 may curve from facing the horizontal direction at a top portion thereof to facing up at a lower portion thereof. The triangular shaped surface 612, the sloping surface 608, and the triangular shaped surface 616 may form a continuous, broad U-shaped surface. Tear-off pins 622 and 624 may be disposed on front casing 604 at which a user may pull to separate the front casing 604 from the rear casing 412. Referring to FIG. 7, a protruding plate 710 may be disposed in front casing 604. The protruding plate 710 may be positioned in such a manner as to guide the film 206 that is being conveyed into the film receiving canister 204. In some embodiments, the protruding plate 710 may provide additional tension to the film 206 to hold the film 206 tightly on the lens 108.

Figure 9:
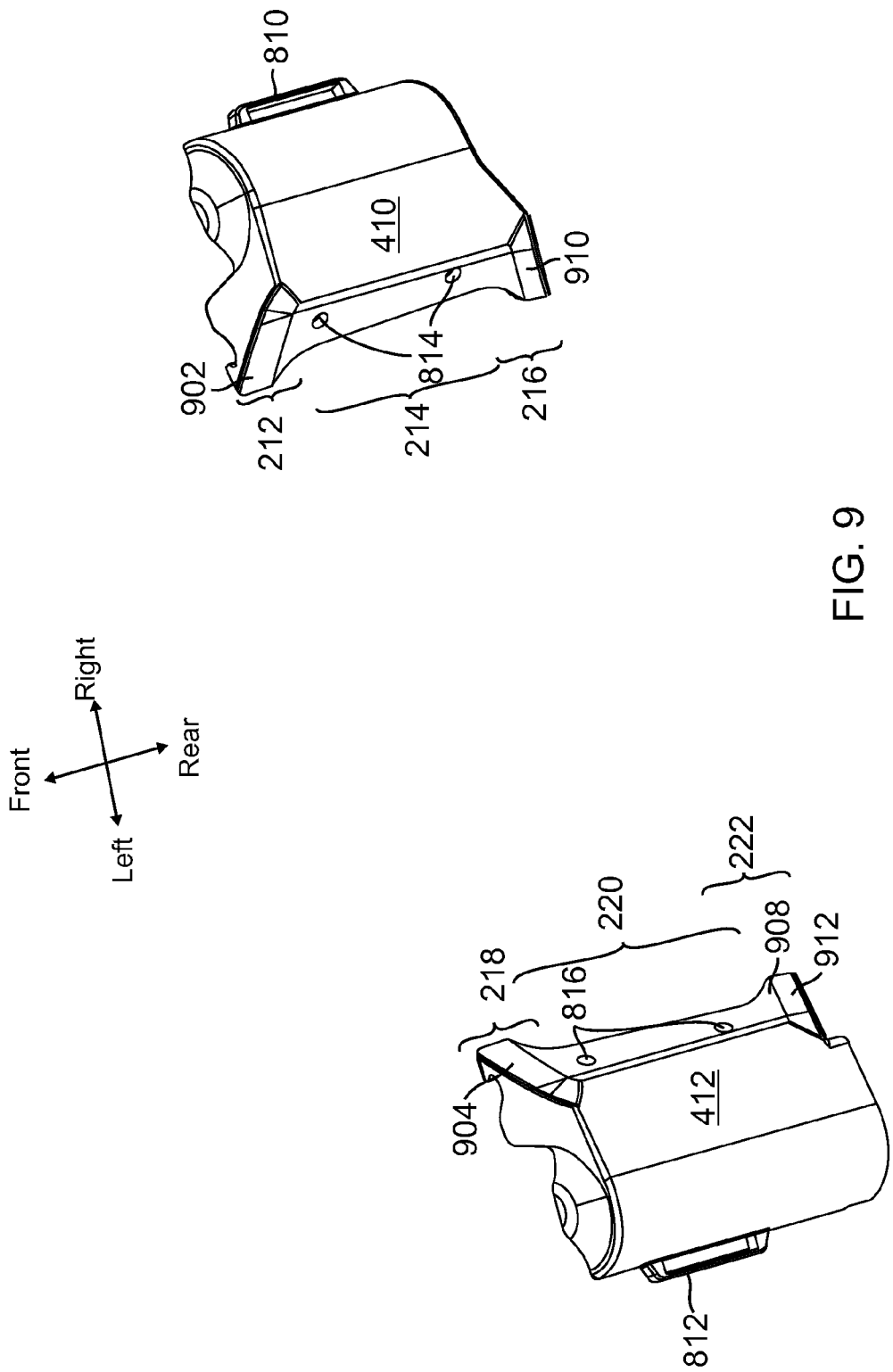
FIG. 9 shows a perspective rear view of the rear casings of FIG. 8, in accordance with an embodiment.

FIGS. 8 and 9 show perspective front and rear views of rear casings, in accordance with an embodiment. As shown in FIG. 8, rear casing 410 may include a side loop 810 configured to receive and retain the coupling mechanism 616 of front casing 602. For example, the deformable hook of the coupling mechanism 616 may be inserted through the side loop 810 to couple the front casing 602 to the rear casing 410. The deformable hook may hook onto the loop 810 to retain the front casing 602 to the rear casing 410. The rear casing 410 also may include two lens attachment openings 814 through which the lens attachment mechanism 310 may be inserted.

Similarly, rear casing 412 may include a side loop 812 configured to receive and retain the coupling mechanism 618 of front casing 604. For example, the deformable hook of the coupling mechanism 618 may be inserted through the side loop 812 to couple the front casing 604 to the rear casing 412. The deformable hook may hook onto the loop 812 to retain the front casing 604 to the rear casing 412. The rear casing 412 also may include two lens attachment openings 816 through which the lens attachment mechanism 312 may be inserted.

Referring to FIG. 9, the upper wing portion 212 of the rear casing 410 may include an upper frame contacting surface 902. The upper frame contacting surface 902 may have a contour substantially conforming to the area of the goggle frame 106 or adaptor frame 104 where the rear casing 410 contacts. The blade portion 214 of the rear casing 410 may include a lens contacting surface 906. Two lens attachment openings 814 may form through the lens contacting surface 906. The lens contacting surface 906 may have a contour substantially conforming to the area of the lens 108 where the rear casing 410 contacts. The lower wing portion 216 of the rear casing 410 may include a lower frame contacting surface 910. The lower frame contacting surface 910 may have a contour substantially conforming to the area of the goggle frame 106 or adaptor frame 104 where the rear casing 410 contacts.

The upper wing portion 218 of the rear casing 412 may include an upper frame contacting surface 904. The upper frame contacting surface 904 may have a contour substantially conforming to the area of the goggle frame 106 or adaptor frame 104 where the rear casing 412 contacts. The blade portion 220 of the rear casing 412 may include a lens contacting surface 908. Two lens attachment openings 816 may form through the lens contacting surface 908. The lens contacting surface 908 may have a contour substantially conforming to the area of the lens 108 where the rear casing 412 contacts. The lower wing portion 222 of the rear casing 412 may include a lower frame contacting surface 912. The lower frame contacting surface 912 may have a contour substantially conforming to the area of the goggle frame 106 or adaptor frame 104 where the rear casing 412 contacts.

Figure 10:
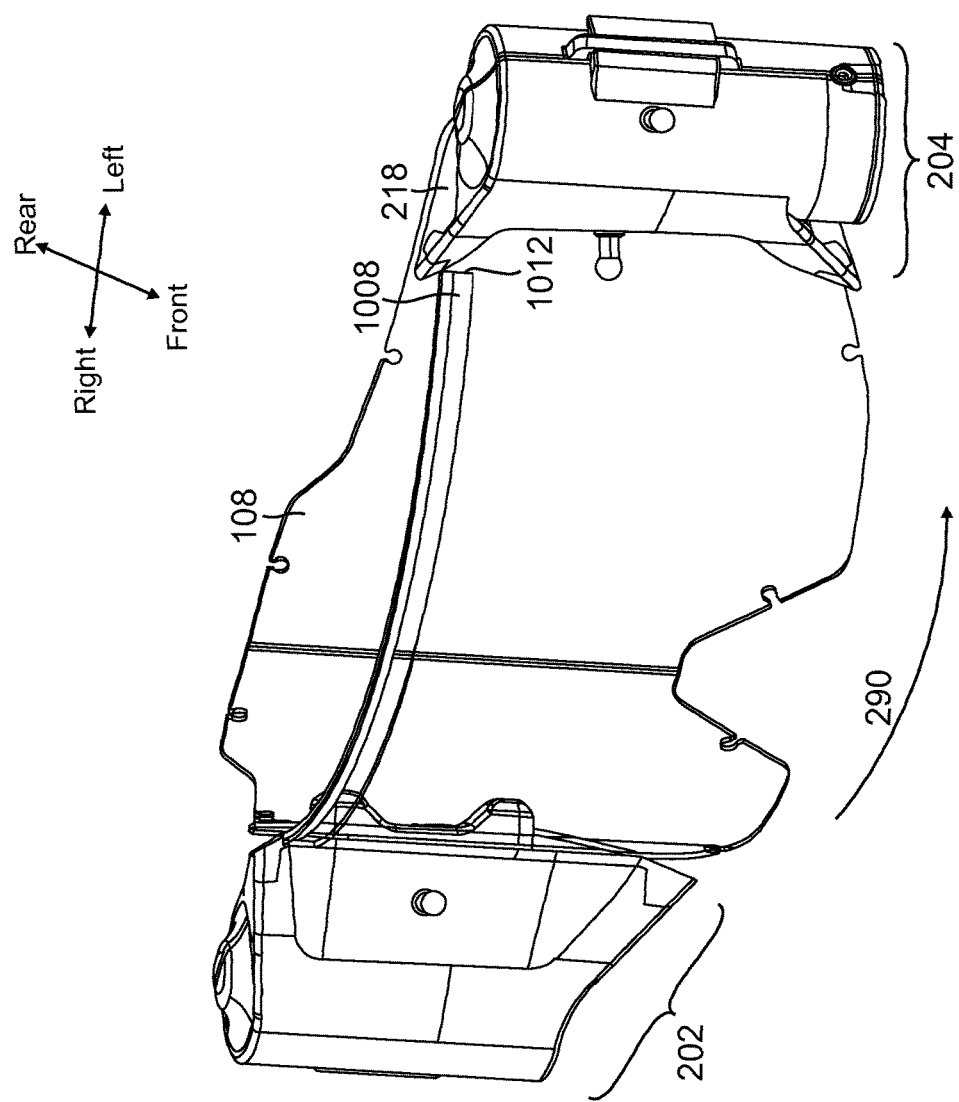
FIG. 10 shows a perspective front view of a roll-off film system attached to a lens, in accordance with an embodiment.
Figure 11:
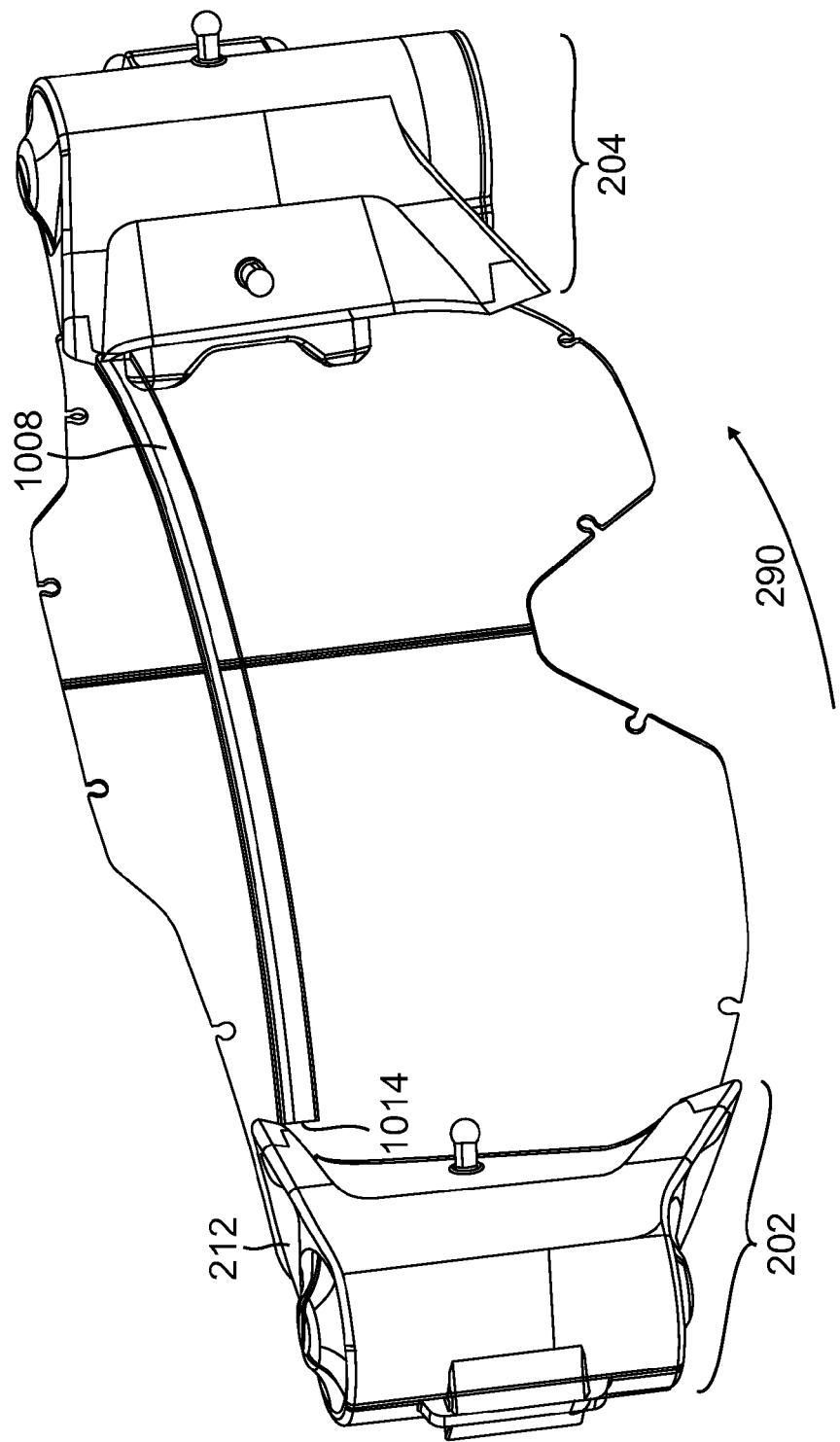
FIG. 11 shows another perspective front view of the roll-off film system attached to the lens of FIG. 10, in accordance with an embodiment.

FIGS. 10 and 11 show perspective front views of a roll-off film system attached to a lens, in accordance with an embodiment. Lens 108 may include a mud flap 1008 disposed on and across the front-top portion of the lens 108. The mud flap 1008 may prevent dirt or mud from dripping down and entering between the film 206 and the front surface of the lens 108. As shown in FIG. 10, the upper wing portion 218 of the film receiving canister 204 may extend over a right end portion 1012 of the mud flap 1008. Thus, the upper wing portion 218 may prevent mud from entering between the mud flap 1008 and the film receiving canister 204 and dripping downward into the film 206. Similarly, as shown in FIG. 11, the upper wing portion 212 of the film dispensing canister 202 may extend over the left end portion 1014 of the mud flap 1008. Thus, the upper wing portion 212 may prevent mud from entering between the mud flap 1008 and the film dispensing canister 202 and dripping downward into the film 206. Accordingly, the upper wing portions 212, and 218, the blade portions 214 and 220, the lower wing portions 216 and 222, and the mud flap 1008 may form a barrier surrounding the section of film 206 covering the lens 108 to prevent mud or dirt from entering between the film 206 and the lens 108.

Figure 12:
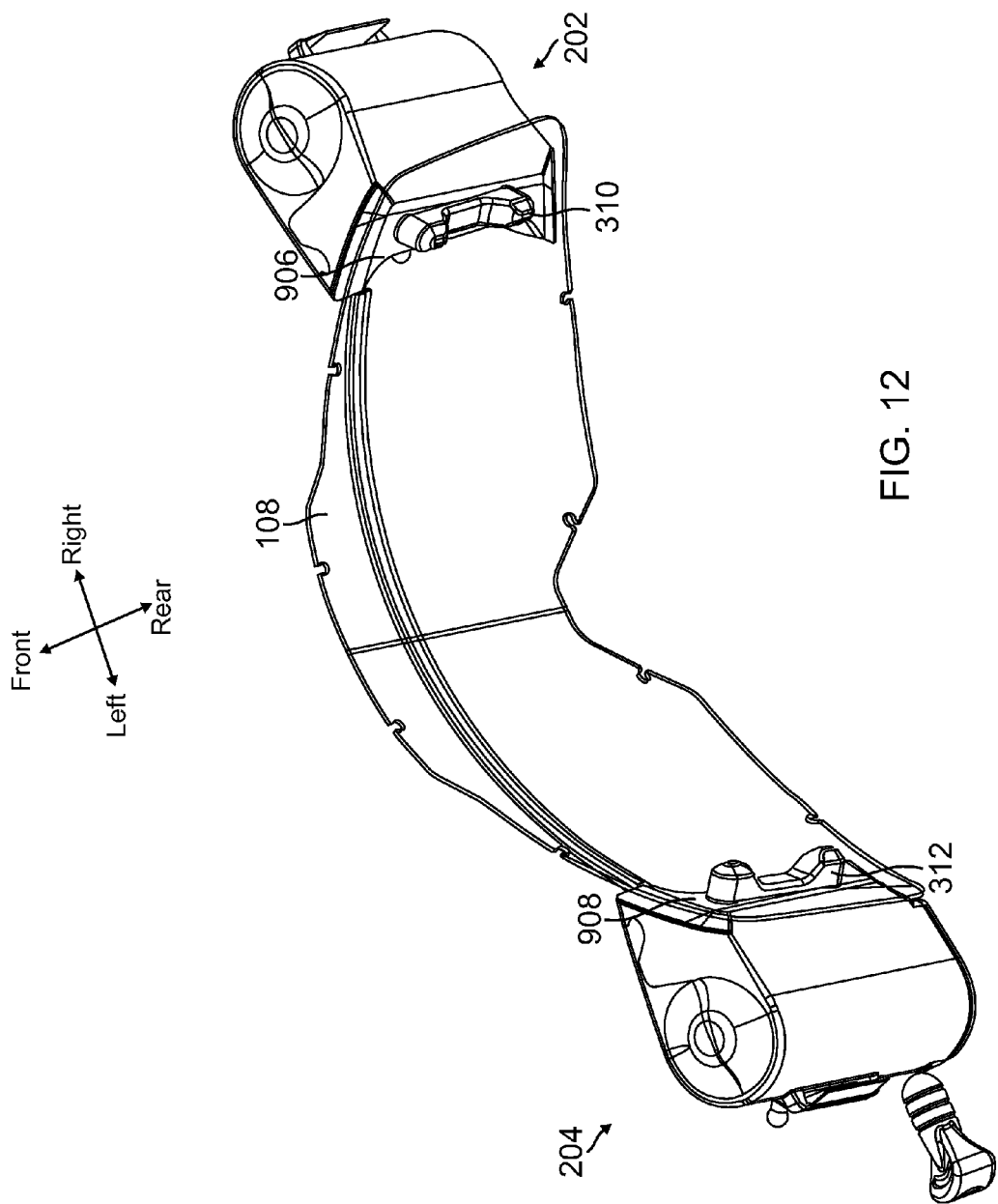
FIG. 12 shows a perspective rear view of the roll-off film system attached to the lens of FIG. 10, in accordance with an embodiment.

FIG. 12 shows a perspective rear view of the roll-off film system attached to the lens of FIG. 10, in accordance with an embodiment. Film dispensing canister 202 may be attached to the lens 108 by lens attachment mechanism 310. The lens attachment mechanism 310 may include a strap with pins on both ends of the strap. The pins may be inserted through two openings in the lens 108 to fasten the strap through the openings to the film dispensing canister 202. The lens contacting surface 906 of the film dispensing canister 202 may have a contour substantially conforming to that of the lens 108 to seamlessly contact the lens 108. Similarly, film receiving canister 204 may be attached to the lens 108 by lens attachment mechanism 312. The lens attachment mechanism 312 may include a strap with pins on both ends of the strap. The pins may be inserted through two openings in the lens 108 to fasten the strap through the openings to the film receiving canister 204. The lens contacting surface 908 of the film receiving canister 204 may have a contour substantially conforming to that of the lens 108 to seamlessly contact the lens 108.

Figure 13:
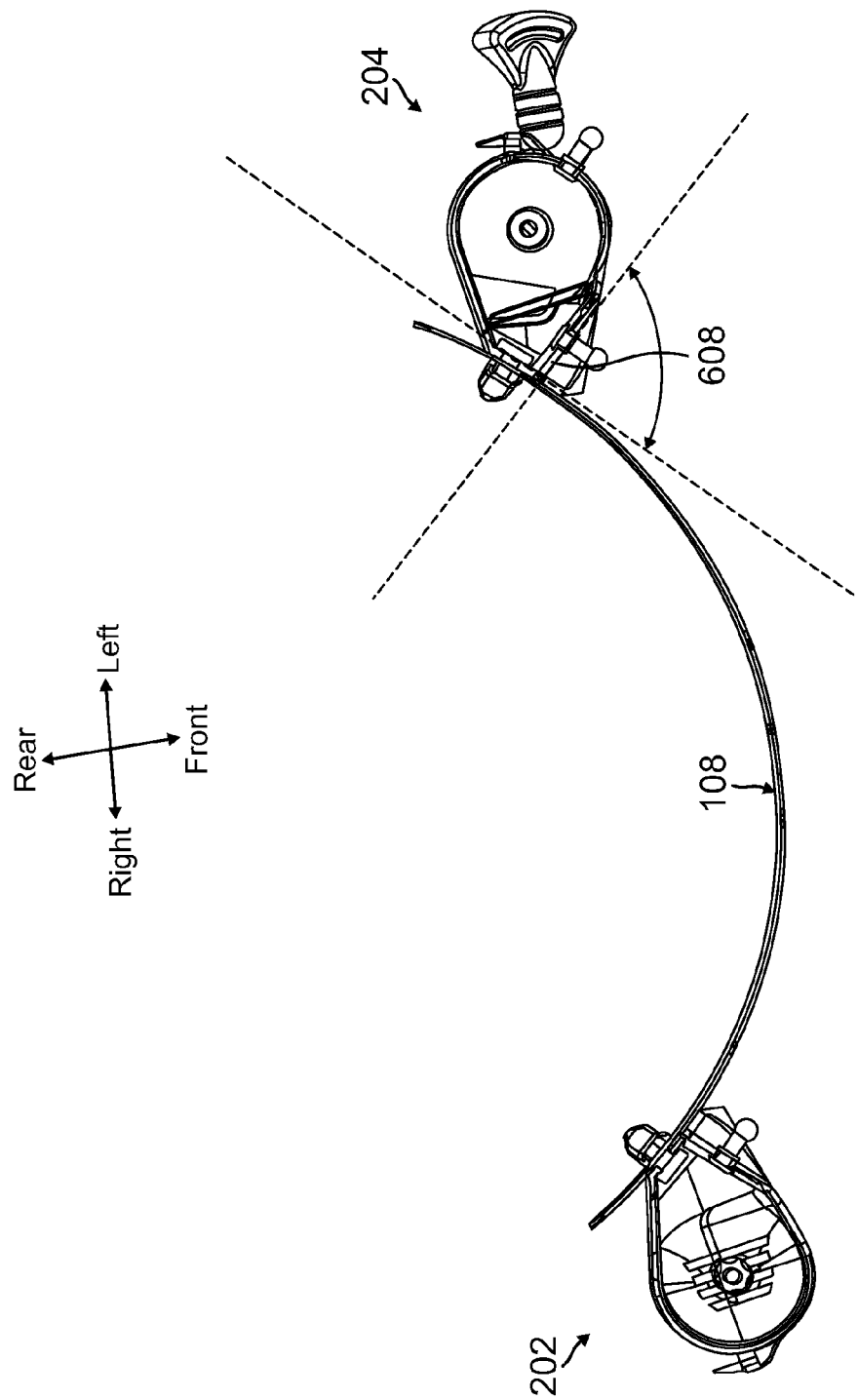
FIG. 13 shows a perspective top view of the roll-off film system attached to the lens of FIG. 10, in accordance with an embodiment.

Referring to FIG. 13, the sloping surface 608 of the blade portion 220 of the film receiving canister 204 may form an obtuse angle with the front surface of the lens 108. As such, dirt or mud collected on the film 206 may be removed and collected on the sloping surface 608 of the blade portion 220 when the film 206 is conveyed through the blade portion 220 into the film receiving canister 204. This may effectively prevent excess amounts of mud or dirt from entering into the film receiving canister 204 and may prolong the use of the roll-off film system 102.

Figure 14:
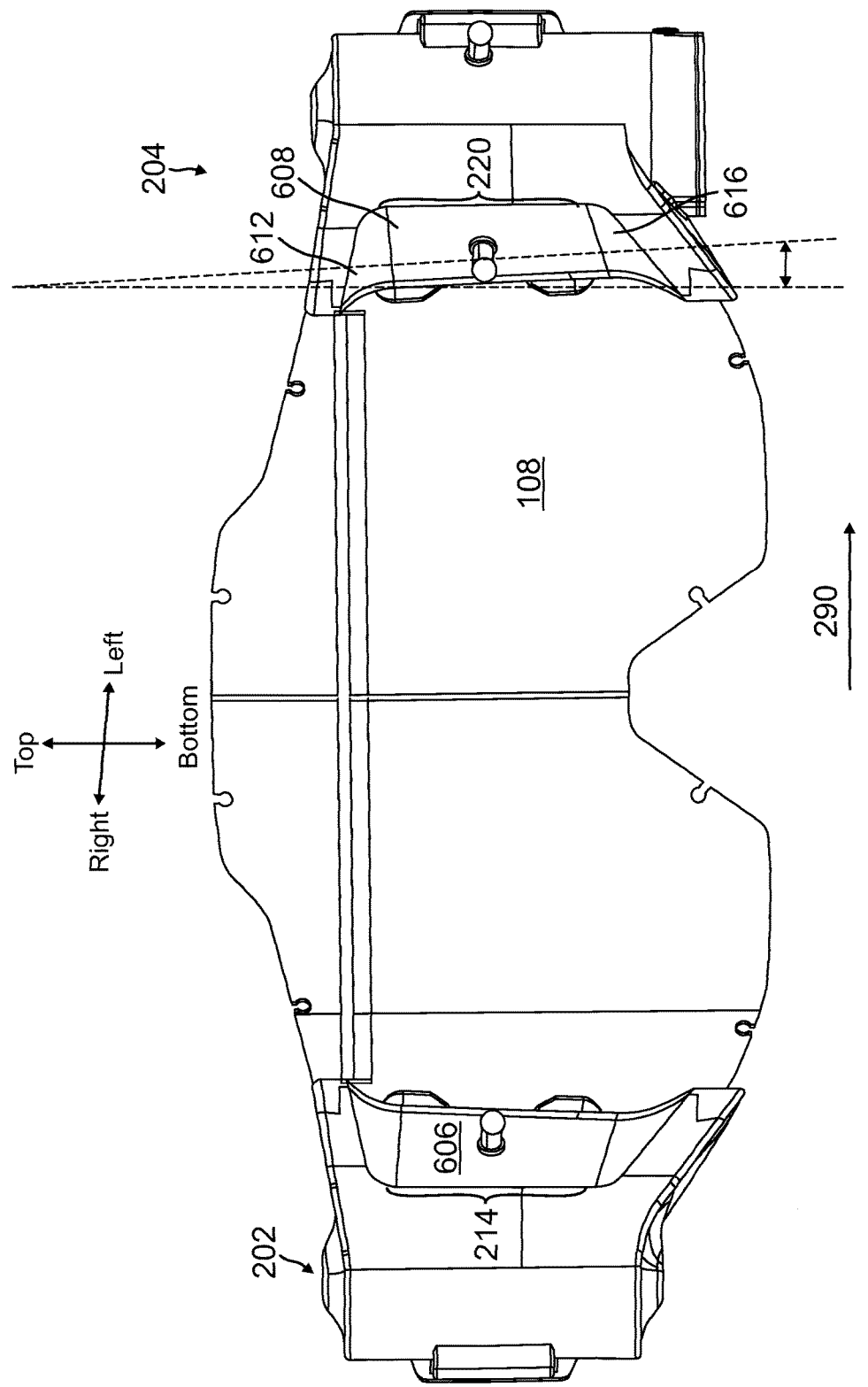
FIG. 14 shows a front view of the roll-off film system attached to the lens of FIG. 10, in accordance with an embodiment.

Referring to FIG. 14, an edge of the sloping surface 608 of the blade portion 220 of the film receiving canister 204 may slant away from the field of view at the lower portion of the edge. Thus, the edge may form an angle with a vertical reference line, such that the upper portion of the edge of the sloping surface 608 may be positioned more upstream in the film conveying direction 290 than the lower portion of the edge of the sloping surface 608. Thus, mud or debris collected on the sloping surface 608 may fall down and be directed away from the field of view, instead of remaining on the sloping surface 608. Similarly, an edge of the sloping surface 606 of the blade portion 214 of the film dispensing canister may slant away from the field of view at the lower portion of the edge. For example, the upper portion of the edge of the sloping surface 606 may be positioned more downstream in the film conveying direction 290 than the lower portion of the edge of the sloping surface 606. Thus, mud or debris collected on the sloping surface 606 may fall down and away from the field of view.

Figure 15:
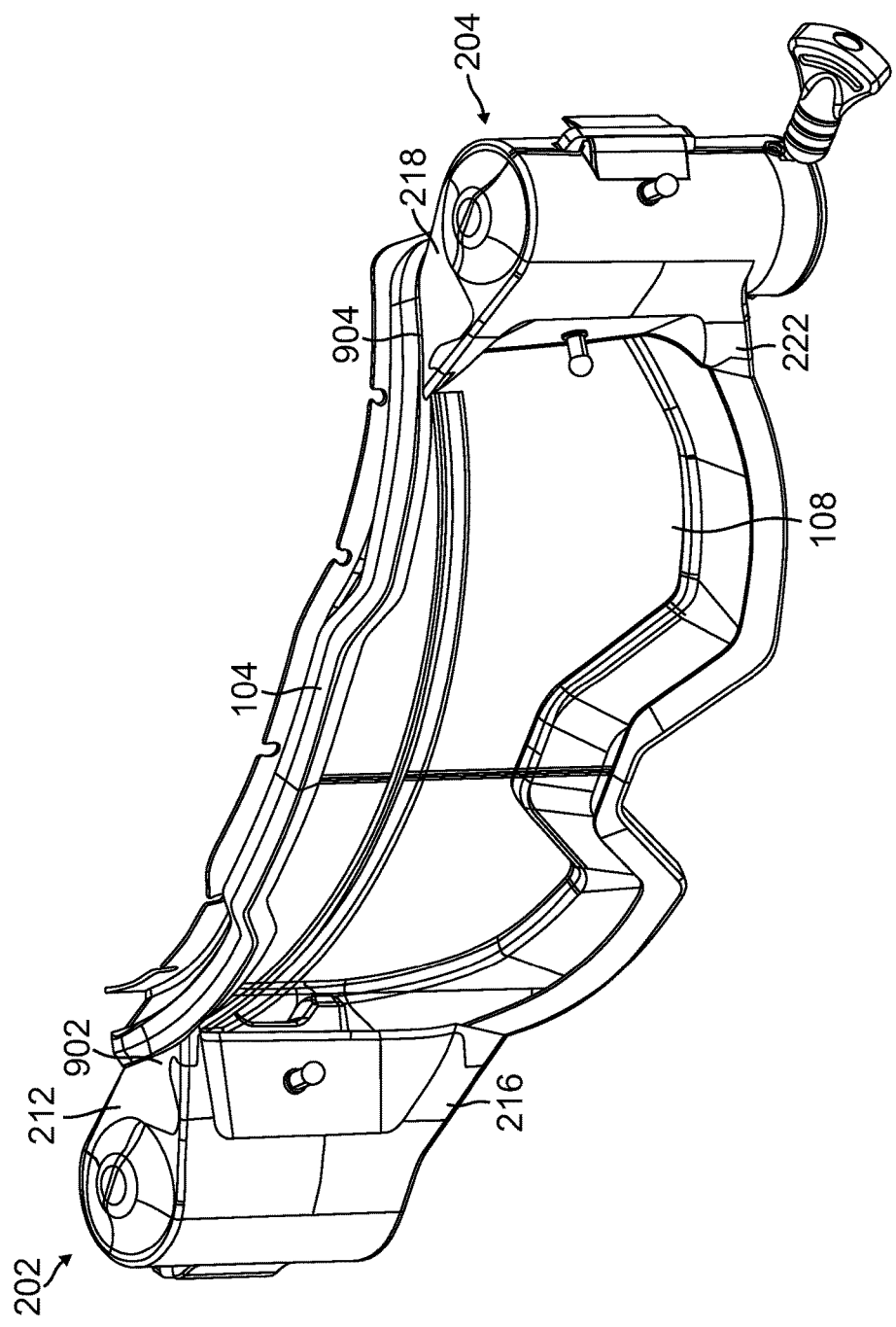
FIG. 15 shows a perspective front view of a roll-off film system attached to an adaptor, in accordance with an embodiment.

FIG. 15 shows a perspective front view of a roll-off film system attached to an adaptor, in accordance with an embodiment. The lens 108 may be installed in the adaptor 104 and the roll-off film system 102 may be installed on the lens 108. As shown in FIG. 15, the frame contacting surface 902 of the upper wing portion 212 may have a contour conforming to that of the adaptor 104 to seamlessly contact the adaptor 104. Similarly, the frame contacting surface 904 of the upper wing portion 218 may have a contour conforming to that of the adaptor 104 to seamlessly contact the adaptor 104. Thus, mud or debris may be prevented from entering through the interface between the roll-off film system 102 and the adaptor 104.

Figure 16:
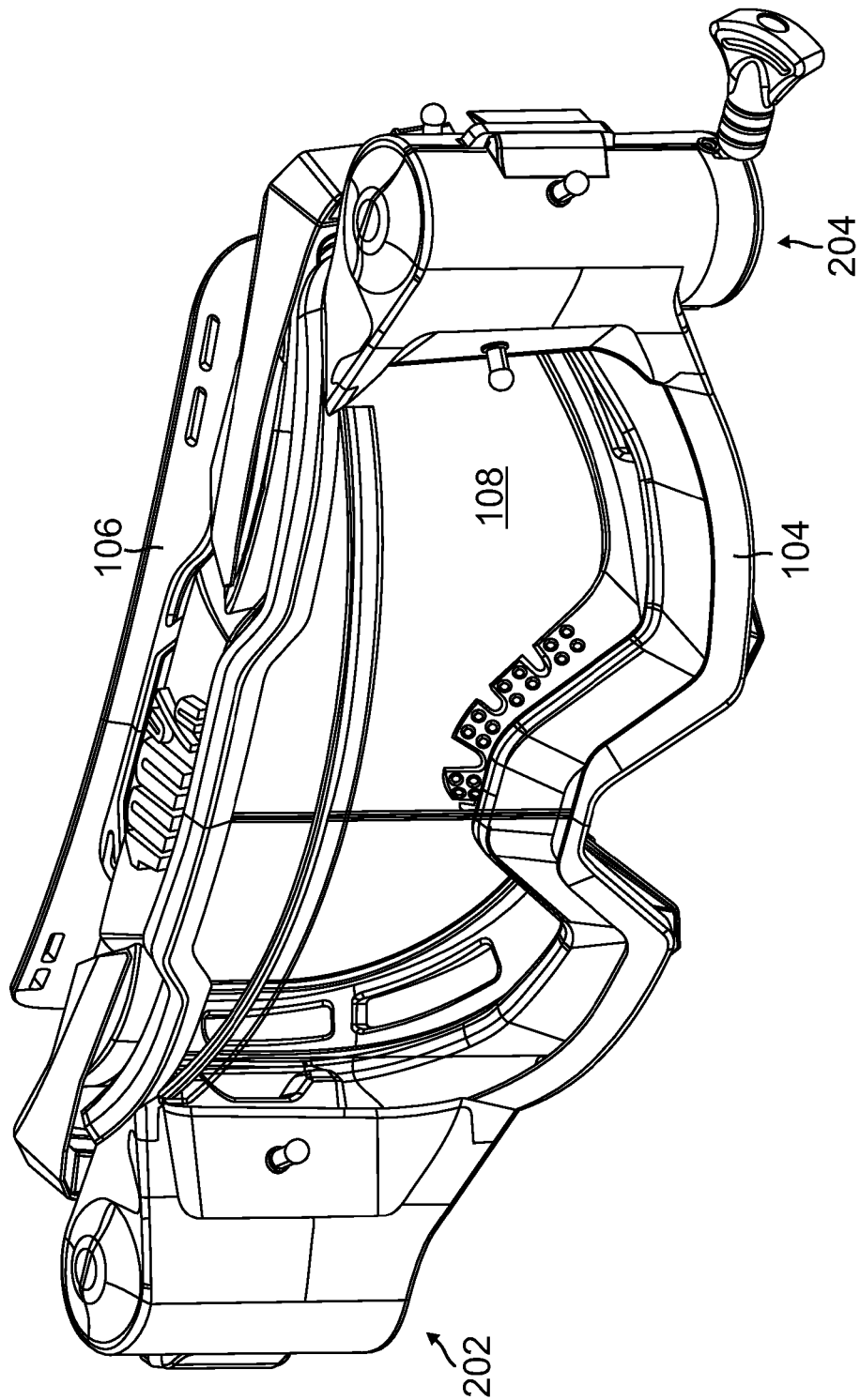
FIG. 16 shows a perspective front view of a roll-off film system attached to an adaptor and a goggle frame, in accordance with an embodiment.

FIG. 16 shows a perspective front view of a roll-off film system attached to an adaptor and a goggle frame, in accordance with an embodiment. The adaptor 104 installed with the roll-off film system 102 may be installed into a goggle frame 106. The adaptor 104 may adapt the goggle frame 106 to use various types of lenses and/or roll-off film systems. For example, the adaptor 104 may adapt the goggle frame 106 to use roll-off film systems of different film sizes, 35 mm film of 40 mm film.

Figure 17:
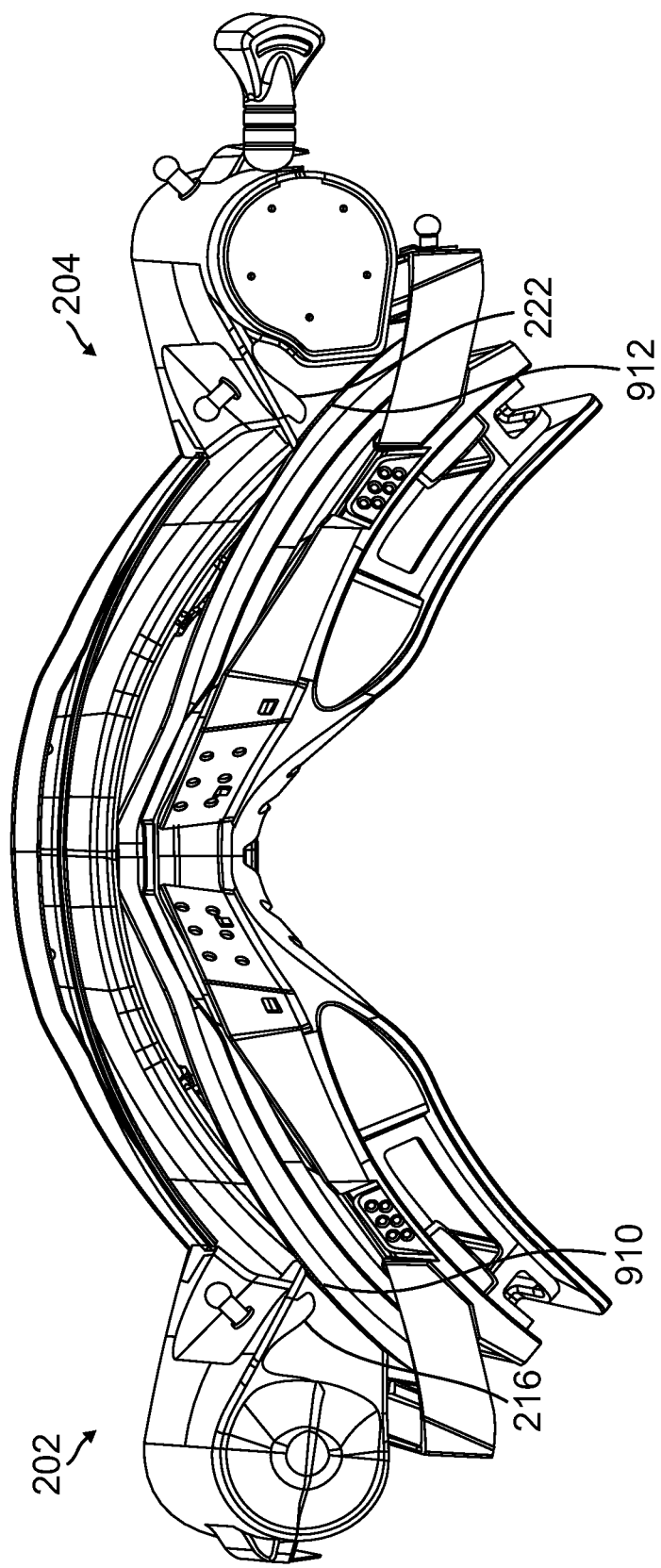
FIG. 17 shows a perspective bottom view of the roll-off film system attached to the adaptor and the goggle frame of FIG. 16, in accordance with an embodiment.

As shown in FIG. 17, the frame contacting surface 910 of the lower wing portion 216 may have a contour conforming to that of the adaptor 104 to seamless contact the adaptor 104. Similarly, the frame contacting surface 912 of the lower wing portion 222 may have a contour conforming to that of the adaptor 104 to seamless contact the adaptor 104. Thus, mud or debris may be prevented from entering through the interface between the roll-off film system 102 and the adaptor 104.

In some embodiments, the roll-off film system 102 may be installed onto the goggle frame 106 without using the adaptor 104. For example, the lens 108 may be installed onto the goggle frame 106 and the adaptor 104 may be attached to the lens 108. The frame contacting surfaces 902, 904, 910, and 912 may respectively conform to the contours of the goggle frame 106 to provide seamless contact between the canisters 202 and 204 and the goggle frame 106 to prevent mud or debris intrusion.

Figure 18:
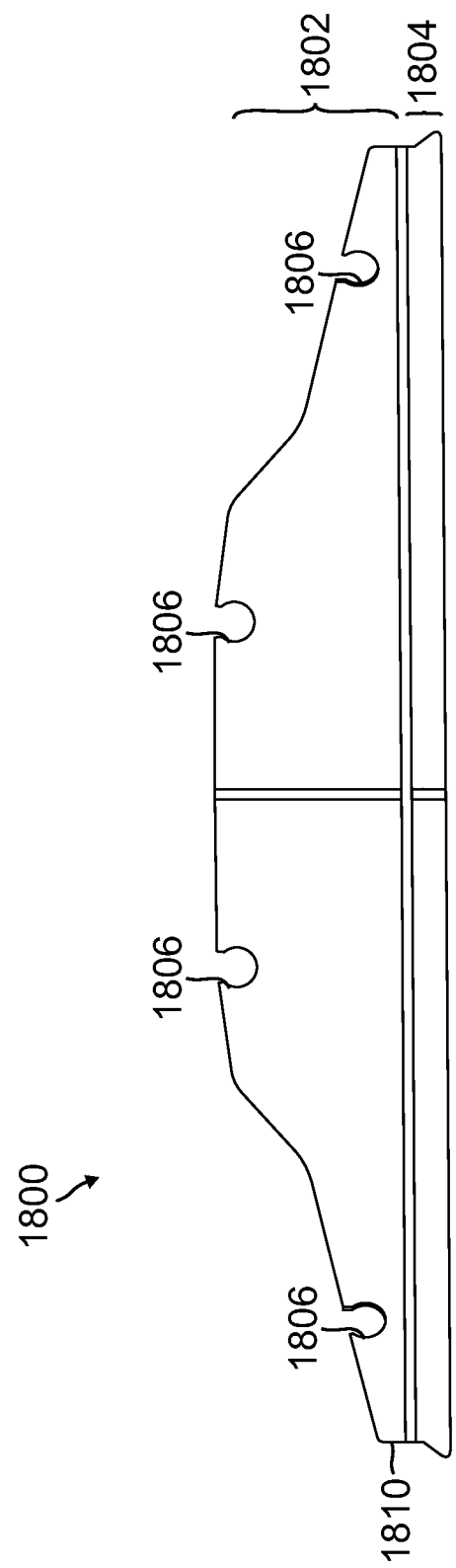
FIG. 18 shows a perspective front view of a mud visor, in accordance with an embodiment.

As noted above, mud flap 1008 may be utilized to prevent mud or debris from entering between roll-off film 206 and goggle lens 108. In some embodiments, mud visors may be utilized in lieu of mud flap 1008 to guard against mud or debris. FIG. 18 shows a perspective front view of a mud visor 1800, in accordance with an embodiment. Mud visor 1800 may be formed of a substantially clear or transparent plastic sheet or plastic film. In some embodiments, mud visor 1800 may be manufactured by plastic stamping from a plastic sheet or film and then thermally molded to have particular contours or bends. As shown in FIG. 18, mud visor may include a lens contacting portion 1802 and a film covering portion 1804. Lens contacting portion 1802 may be an upper portion of mud visor 1800 and the film covering portion 1804 may be a lower portion of mud visor 1800. Lens contacting portion 1802 may be configured to attach to a front and top surface of a goggle lens. As such, a top perimeter of lens contacting portion 1802 may have a contour or shape similar to the top perimeter of the goggle lens 108. Lens contacting portion 1802 also may include cutouts 1806 positioned along the top perimeter corresponding to the positions and shapes of cutouts of the goggle lens 108. As such, lens contacting portion 1802 may match and attach to a top portion of goggle lens 108. When mud visor 1800 is not attached to goggle lens 108, mud visor 1800 may be substantially flat. Mud visor 1800 may be elastic and bendable to form a contour when attached to goggle lens 108 to conform with the curving surface of goggle lens 108.

Figure 19:
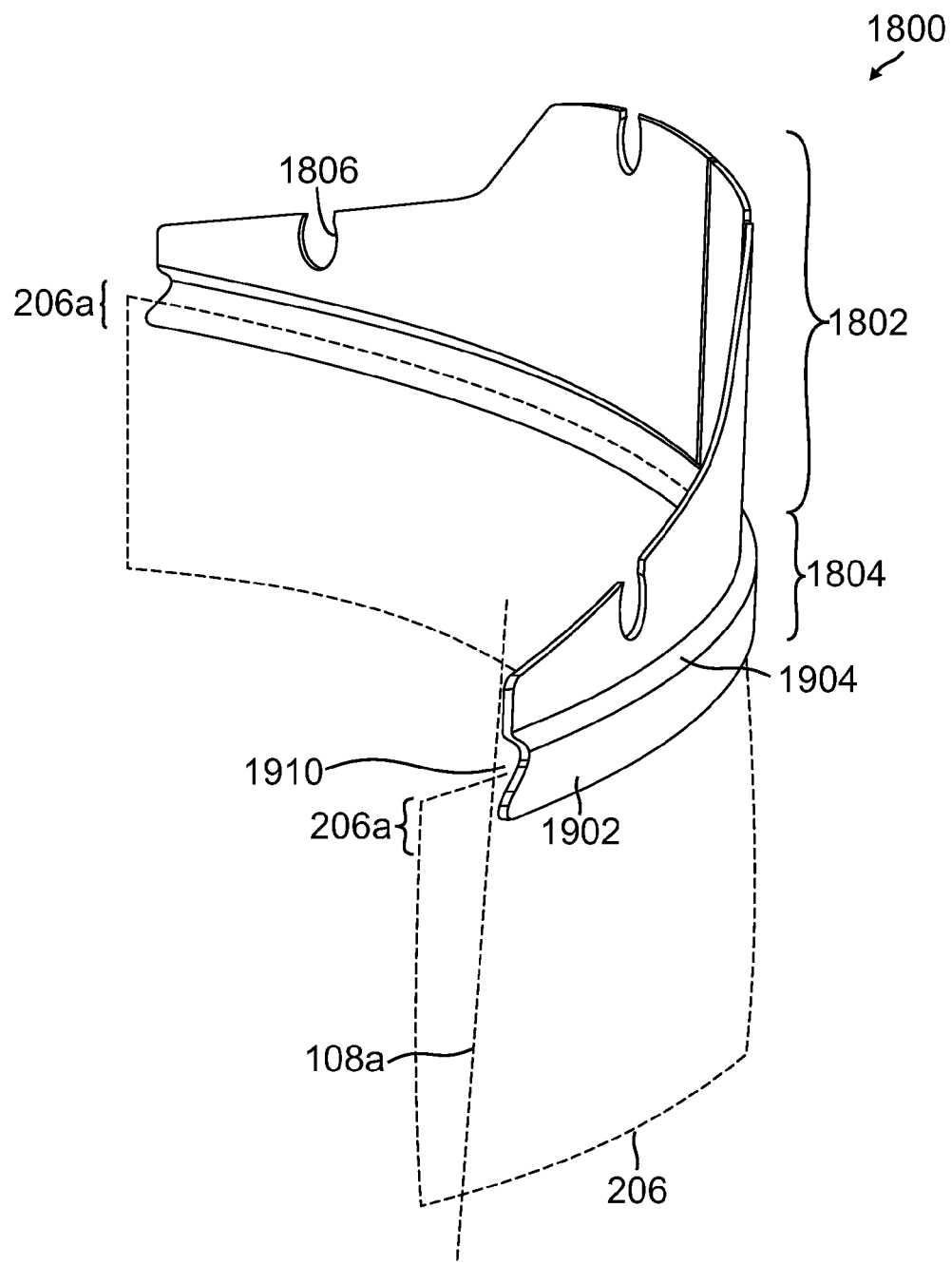
FIG. 19 shows a perspective side view of the mud visor of FIG. 18, in accordance with an embodiment.

FIG. 19 shows a perspective side view of the mud visor of FIG. 18, in accordance with an embodiment. Film covering portion 1804 may have an overhang portion 1904 and a film guiding portion 1902. Overhang portion 1904 may protrude from lens contacting portion 1802 in a forward direction or in a direction away from goggle lens 108 when mud visor 1800 is attached to goggle lens 108. Film guiding portion 1902 may extend back from a distal end of the overhang portion 1902 or in a direction toward goggle lens 108 when mud visor 1800 is attached to goggle lens 108. Film covering portion 1804 may be formed by thermal molding. Film covering portion 1804 may be configured to cover and guide the section of roll-off film 206 (shown in broken line) resting on goggle lens 108. In particular, the overhang portion 1904 may cover the roll-off film 206 from the top side to prevent mud from entering. As shown in FIG. 19, an upper perimeter portion 206a of the roll-off film 206 may be covered by the film covering portion 1804 of mud visor 1800. Film guiding portion 1902 may contact or press the roll-off film 206 onto the front surface 108a of goggle lens 108 to ensure a tight contact between the film covering portion 1804 and the roll-off film 206. An enclosure 1910 may be formed between the film guiding portion 1902, the overhang portion 1904 and the front surface 108a of the goggle lens 108 to accommodate the upper perimeter portion 206a of the roll-off film 206. Further, as the roll-off film 206 is conveyed across the front surface 108a (a portion of which is shown as a broken line for clarity) of goggle lens 108, film covering portion 1804 may guide the top perimeter portion of the roll-off film 206 in a stable path without moving vertically away from the path.

Figure 20:
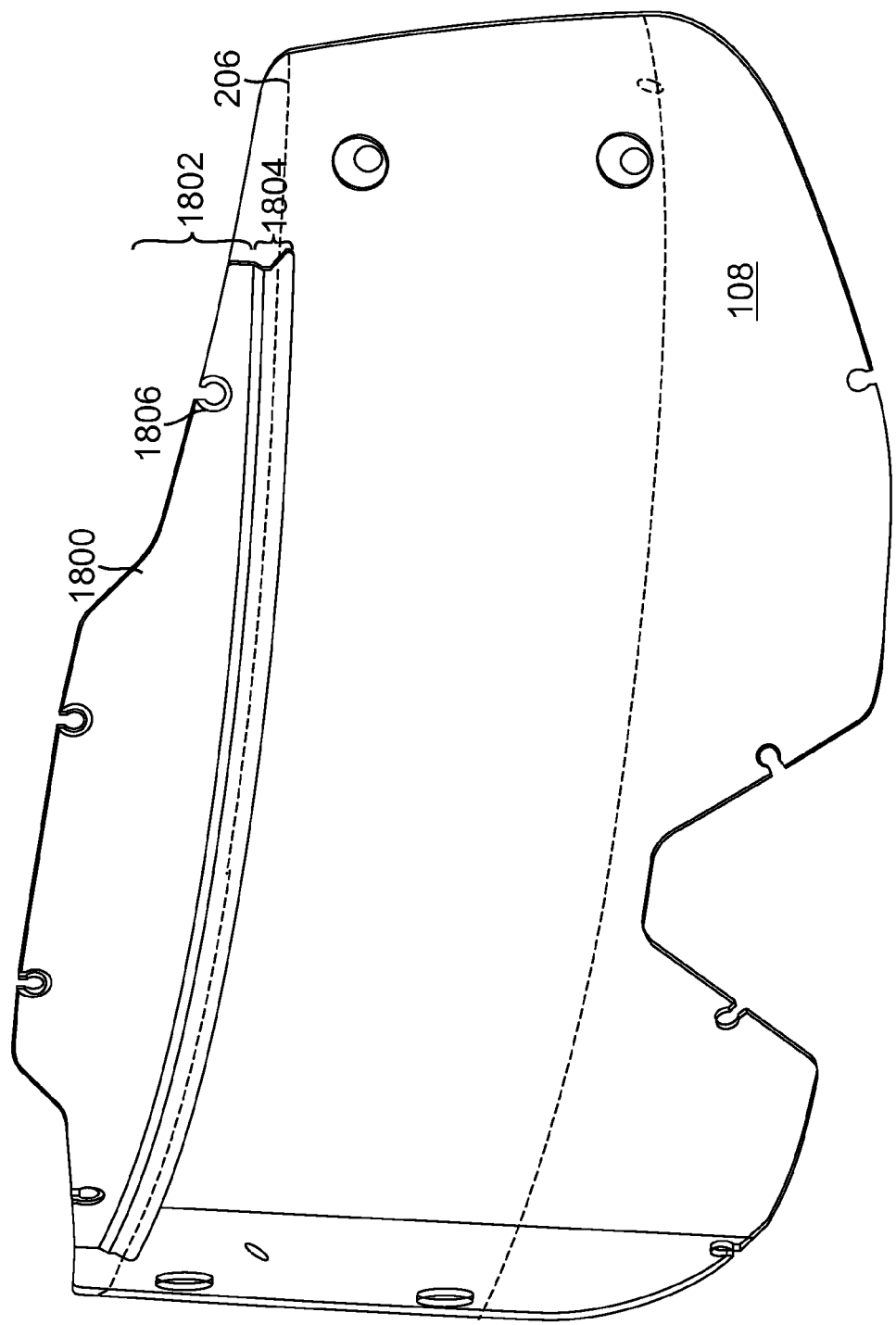
FIG. 20 shows a perspective view of a mud visor attached to a goggle lens, in accordance with an embodiment.

FIG. 20 shows a perspective view of a mud visor attached to a goggle lens, in accordance with an embodiment. As noted above, when mud visor 1800 is attached to lens 108, lens contacting portion 1802 may be bonded to a top, front surface of lens 108. Lens contacting portion 1802 may have a shape or contour that conforms to the shape or contour of lens 108. Lens contacting portion 1802 of mud visor 1800 may include cutouts 1806 that match the positions and shapes of corresponding cutouts on lens 108. Different types of mud visors may be designed and configured for different types of lenses according to their shapes and contours. As shown in FIG. 20, film covering portion 1804 of mud visor 1800 covers a top perimeter portion of the roll-off film 206.

Figure 21:
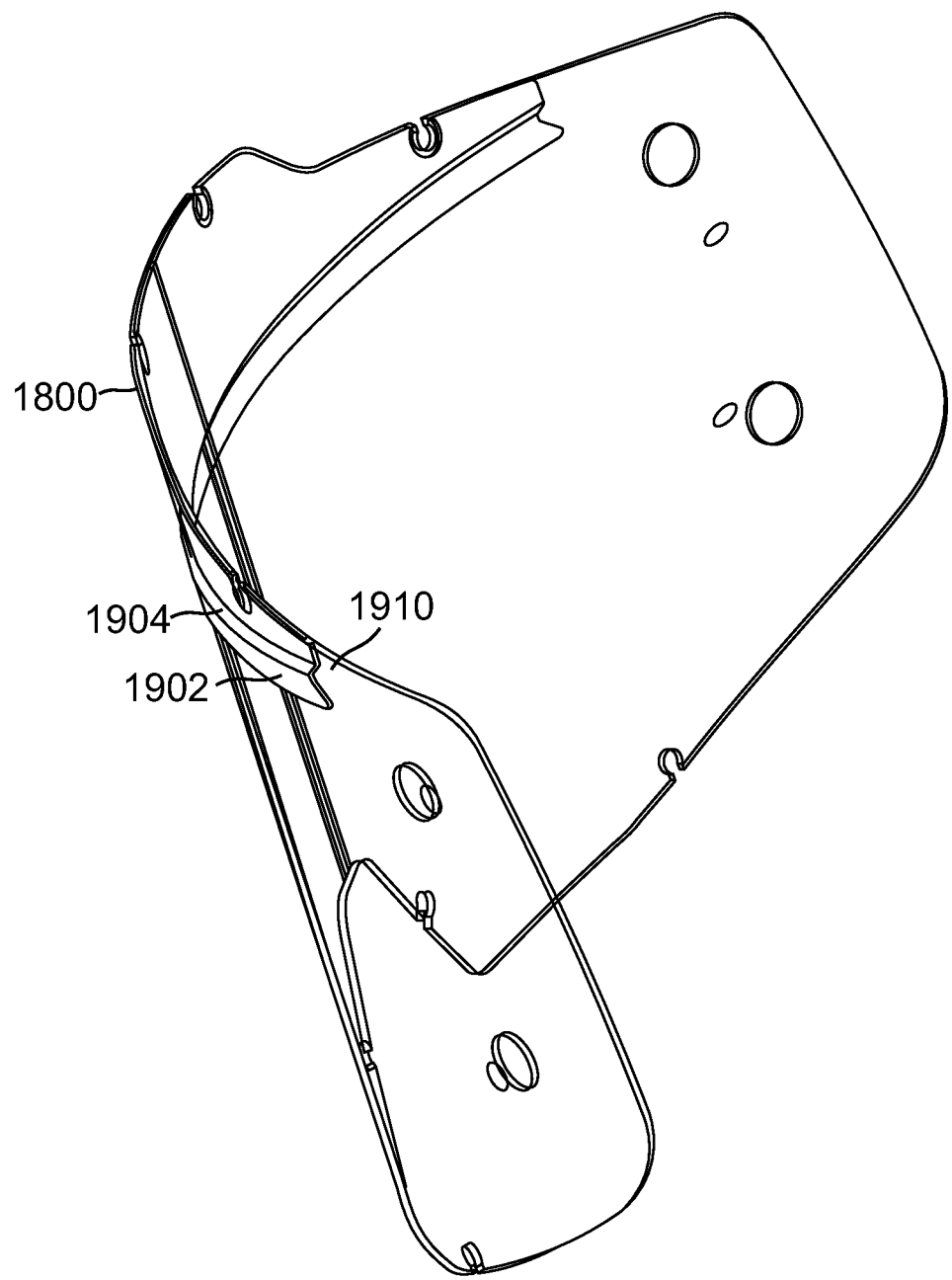
FIG. 21 shows a perspective side view of the mud visor of FIG. 20 attached to the goggle lens, in accordance with an embodiment.

FIG. 21 shows a perspective side view of the mud visor of FIG. 20 attached to the goggle lens, in accordance with an embodiment. Overhang portion 1904 of mud visor 1800 may protrude away from a front surface of lens 108 to form an overhang. Film contacting portion 1902 of mud visor 1800 may extend back from the overhang toward the front surface of lens 108. The overhang shape of film contacting portion 1902 may have a biasing force toward lens 108 when mud visor 1800 is attached to lens 10. As such, film contacting portion 1902 may press a roll-off film 206 onto lens 108. In some embodiments, mud visor 1800 is formed with plastic or an elastic material that may provide the biasing force to press the roll-off film 206.

Figure 22:
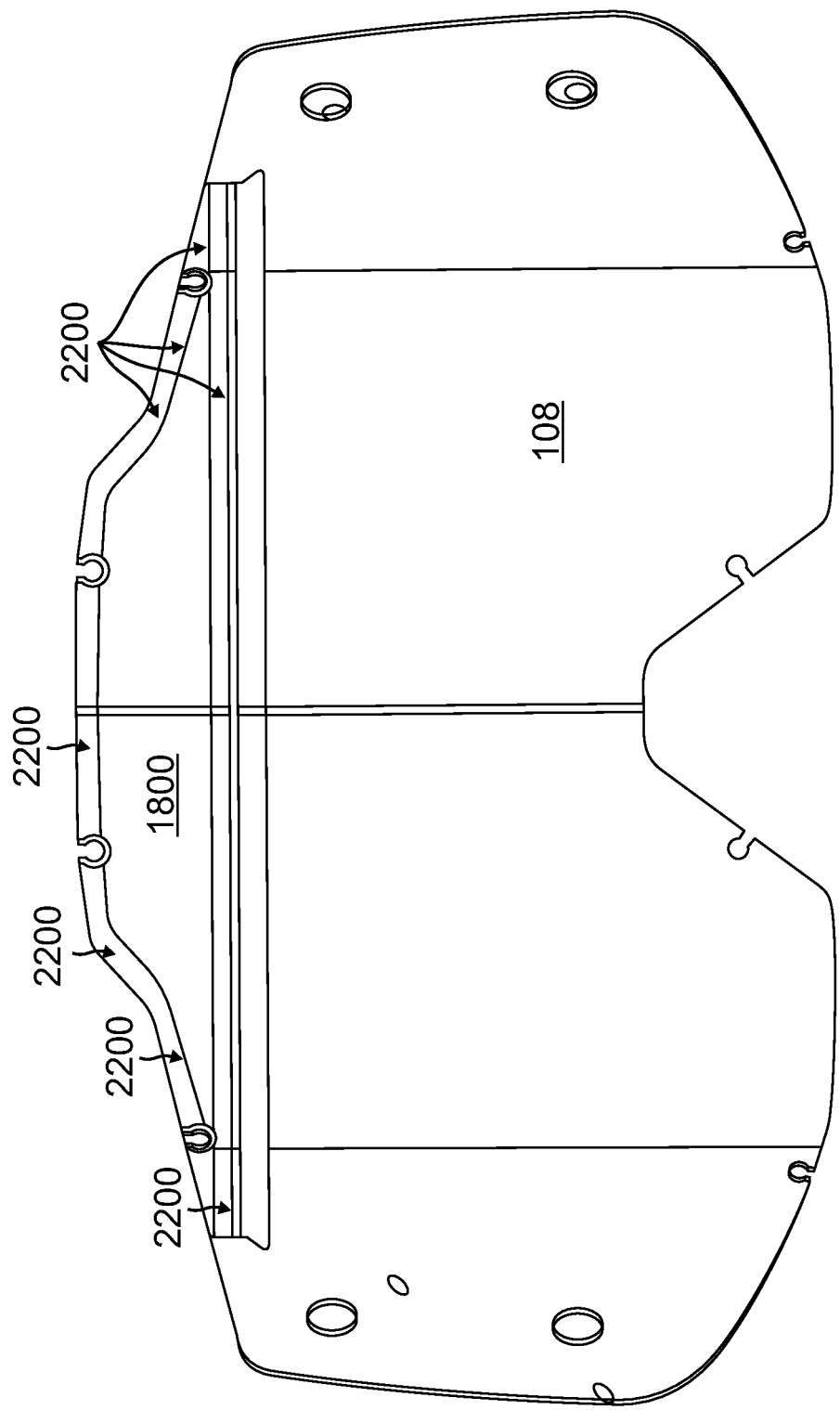
FIG. 22 shows a perspective front view a mud visor attached to a goggle lens with substantially transparent material, in accordance with an embodiment.

FIG. 22 shows a perspective front view of a mud visor attached to a goggle lens with substantially transparent material, in accordance with an embodiment. Mud visor 1800 may be attached to a front surface of lens 108 at the lens contacting portion 1802 by substantially transparent material. For example, in some embodiments, a substantially transparent adhesive may be applied to a backside of lens contacting portion 1802 to attach lens contacting portion 1802 to lens 108. By using a substantially transparent adhesive, the field of view through lens 108 may not be obstructed by the adhesive at mud visor 1800. In some embodiments, substantially transparent adhesive tape may be used to attach lens contacting portion 1802 to lens 108. In particular, the adhesive tape may be applied around the perimeter portion 2200 of lens contacting portion 1802, as shown in FIG. 22. By applying adhesive or adhesive tape only around the perimeter, more area of mud visor 1800 or lens 108 remains visible as part of the user's field of view, and is not obstructed by the adhesive or adhesive tape. Thus, the user's field of view is improved. In another embodiment, the substantially transparent adhesive also may be applied to the center area of the lens contacting portion 1802. In particular, the optical adhesive may allow clear view through the center area.

Figure 23:
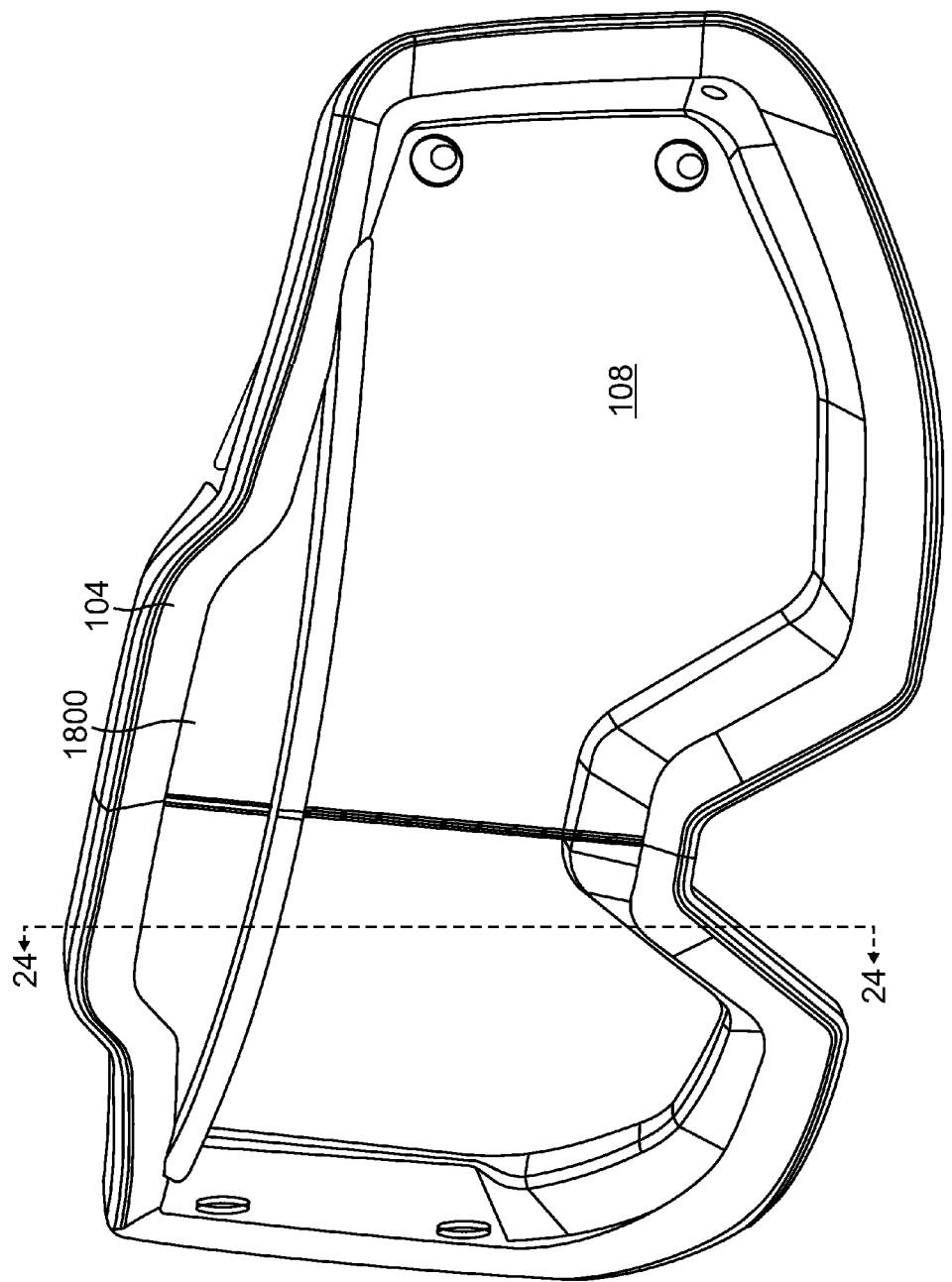
FIG. 23 shows a mud visor attached to a goggle lens which is attached to an adaptor, in accordance with an embodiment.
Figure 24:
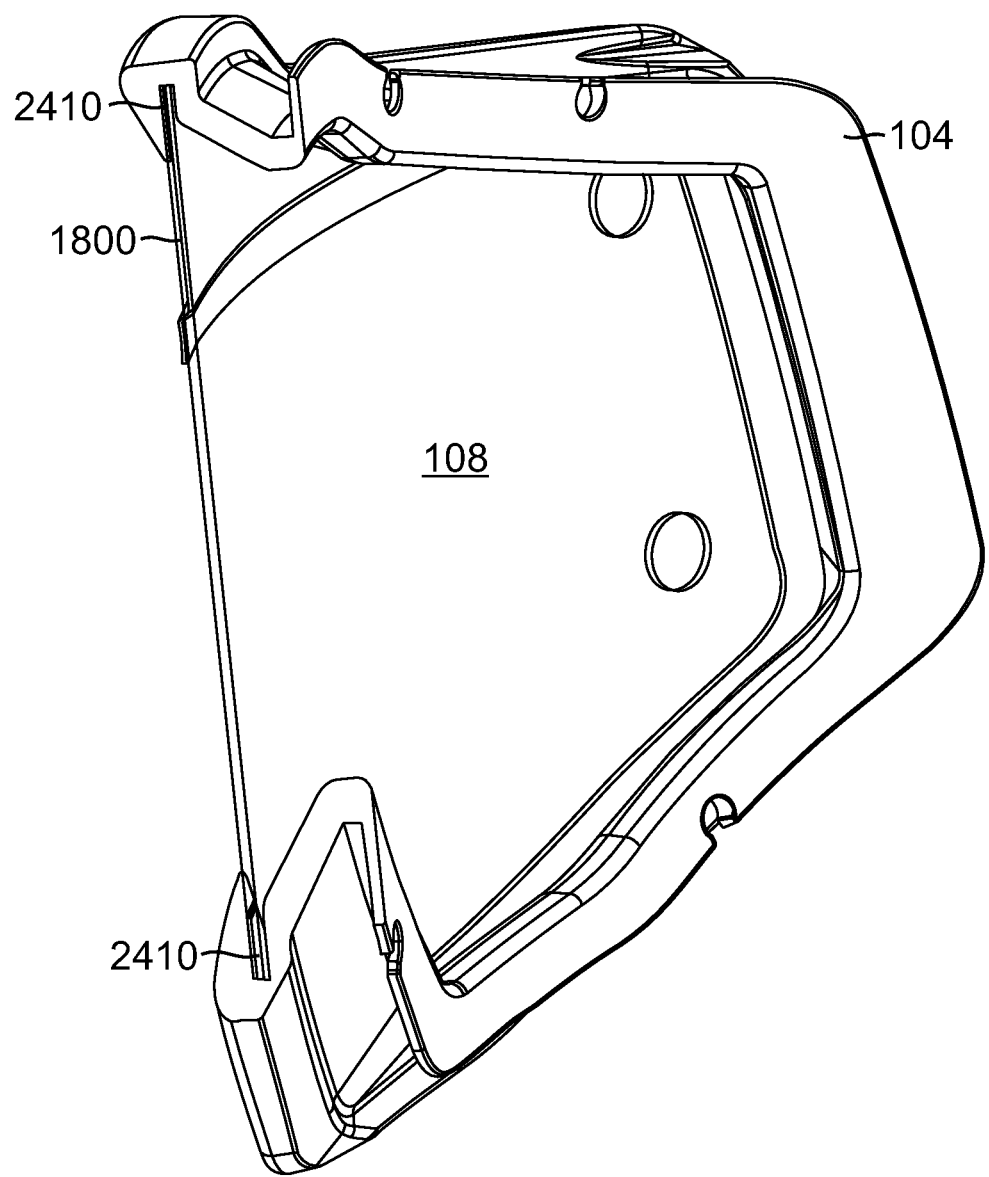
FIG. 24 shows a cross sectional view of the mud visor attached to the goggle lens and the adaptor taken along line 24-24 of FIG. 23, in accordance with an embodiment.

FIG. 23 shows a mud visor attached to a goggle lens which is attached to an adaptor, in accordance with an embodiment. Lens 108 attached with mud visor 1800 may be inserted into a lens groove 2410 (See FIG. 24) of adaptor 104 because mud visor 1800 is formed by a substantially thin plastic film or plastic sheet. Adaptor 104 may then be attached to a goggle frame 106. In some embodiments, lens 108 attached with mud visor 1800 may be attached directly to a lens groove 2410 of goggle frame 106 without adaptor 104. FIG. 24 shows a cross sectional view taken along line 24-24 of FIG. 23, in accordance with an embodiment. As shown in FIG. 24, a top portion of lens 108 and a top portion of mud visor 1800 are both inserted into the lens groove 2410 of adaptor 104. In a case where adaptor 104 is not used, both the top portion of lens 108 and the top portion of mud visor 1800 may be inserted into the lens groove 2410 of goggle frame 106. Because mud visor 1800 is inserted into the lens groove 2410, mud or liquid may be prevented from entering between mud visor 1800 and lens 108 from the top side.

Figure 25:
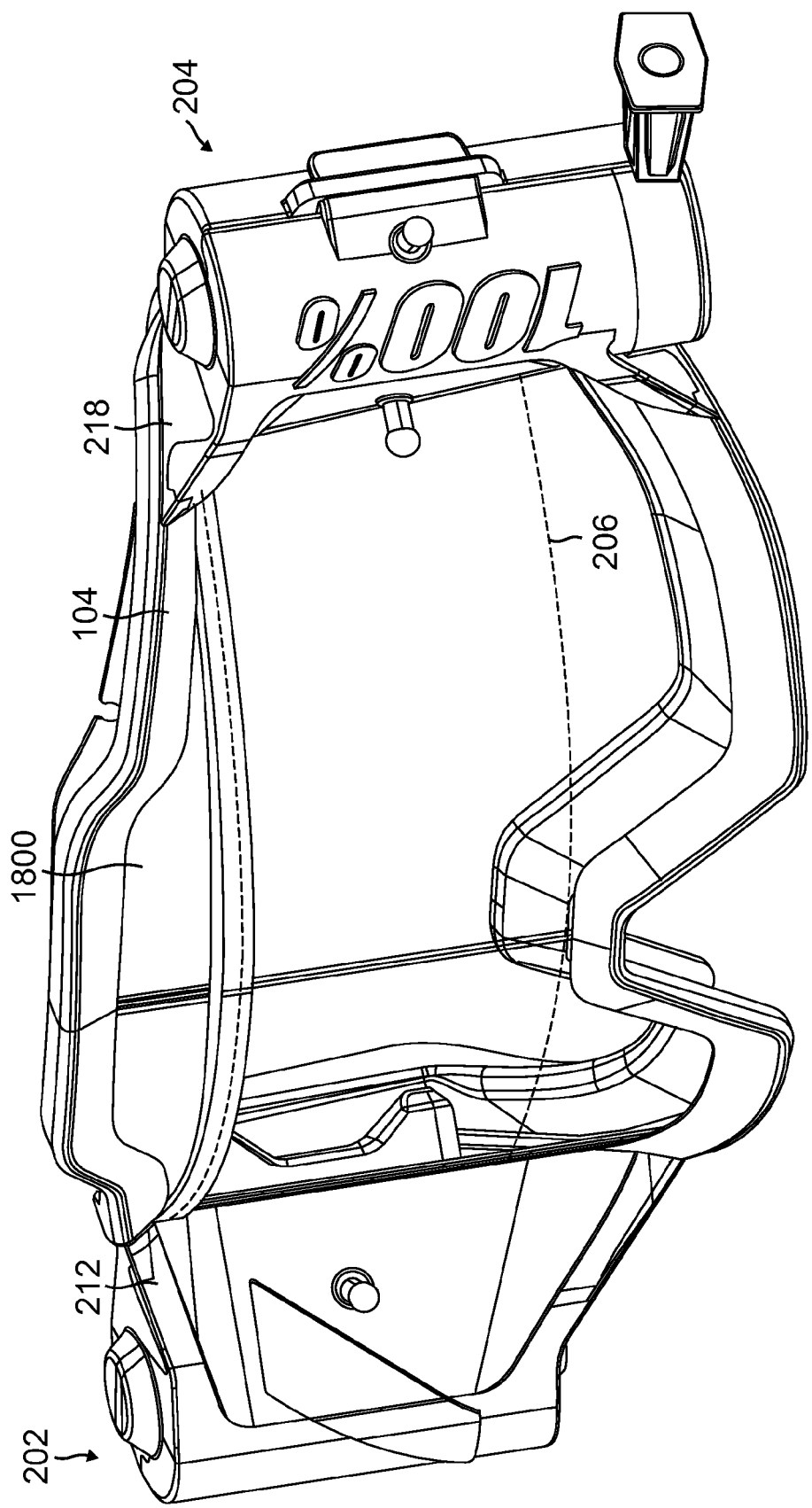
FIG. 25 shows a perspective view of a mud visor and a roll-off film system attached to a lens and an adaptor, in accordance with an embodiment.

FIG. 25 shows a perspective view of a mud visor and a roll-off film system attached to a lens and an adaptor, in accordance with an embodiment. Mud visor 1800 may extend horizontally across lens 108 to reach both film dispensing canister 202 and film receiving canister 204. In particular, as shown in FIG. 25, upper wing portion 218 of film receiving canister 204 may cover an end portion 1810 of mud visor 1800. Similarly, upper wing portion 212 of film dispending canister 202 may cover the other end portion of mud visor 1800. In particular, both end portions of film covering portion 1804 may transition from the overhang shape to a flat shape to fit under the respective upper wing portions 212 and 218 of film dispending canister 202 and film receiving canister 204. This may allow seamless coverage of mud visor 1800 from the film dispending canister 202 to film receiving canister 204.

Figure 26:
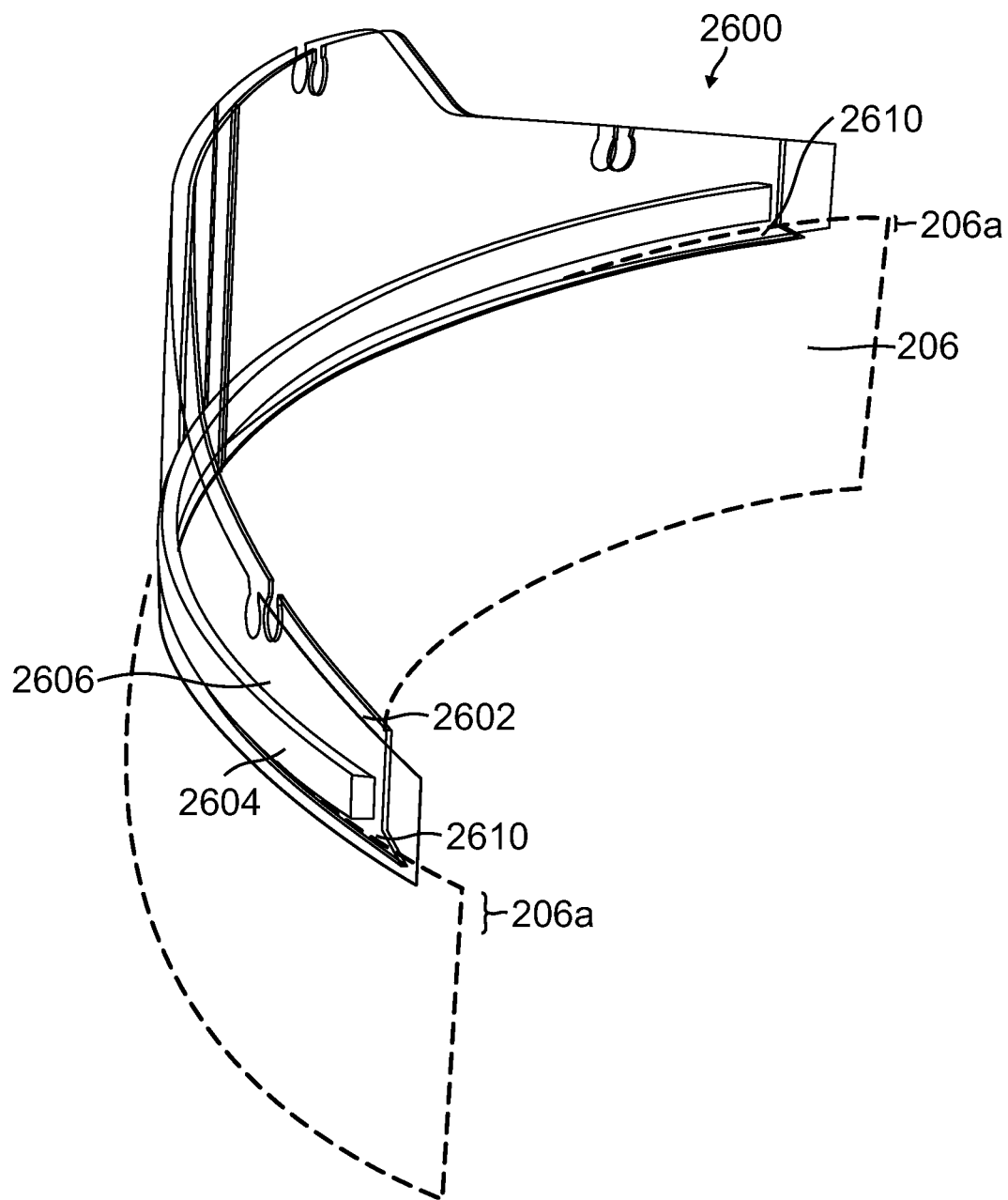
FIG. 26 shows a perspective view of a double-layer mud visor, in accordance with an embodiment.
Figure 27:
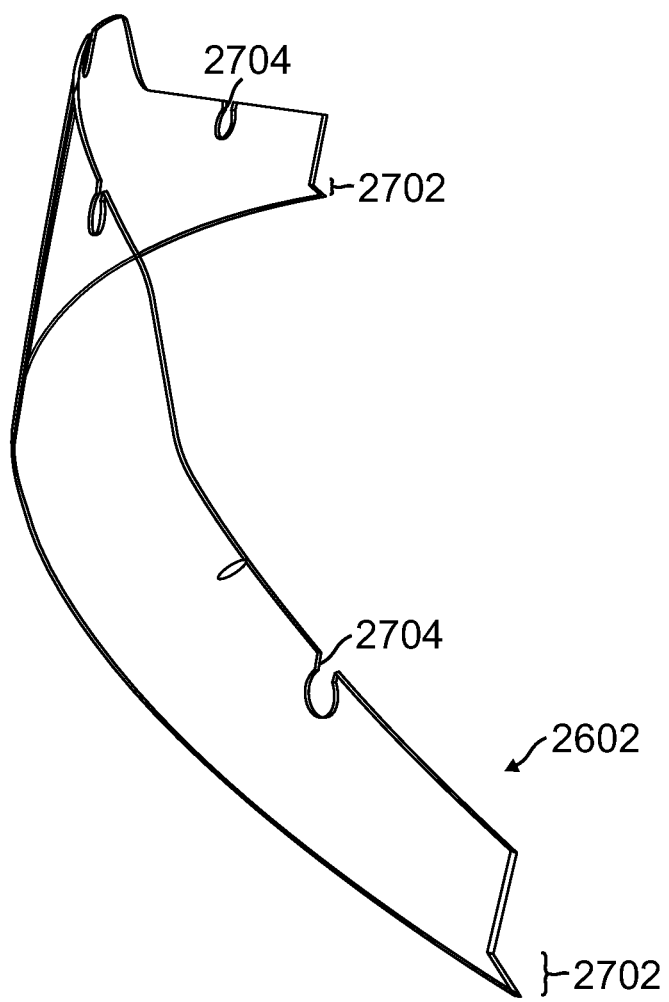
FIG. 27 shows a perspective view of an inner layer of the double-layer mud visor of FIG. 26, in accordance with an embodiment.

FIG. 26 shows a perspective view of another mud visor, in accordance with an embodiment. Mud visor 2600 may include an inner layer 2602 and an outer layer 2606 in a double layer configuration. A spacer 2604 is disposed between inner layer 2602 and outer layer 2602. Inner layer 2602 and outer layer 2606 may both be formed with plastic films or plastic sheets by plastic stamping with thermally molding. FIG. 27 shows a perspective view of an inner layer of the double-layer mud visor of FIG. 26, in accordance with an embodiment. As shown in FIG. 27, inner layer 2602 may have a substantially similar shape and/or contour as that of a top portion of goggle lens 108. Lower, corner portions 2702 of inner layer 2602 may have bends and configured to guide roll-off film. Cutouts 2704 also are provided along the top perimeter of inner layer 2602 to match cutouts of lens 108.

Figure 28:
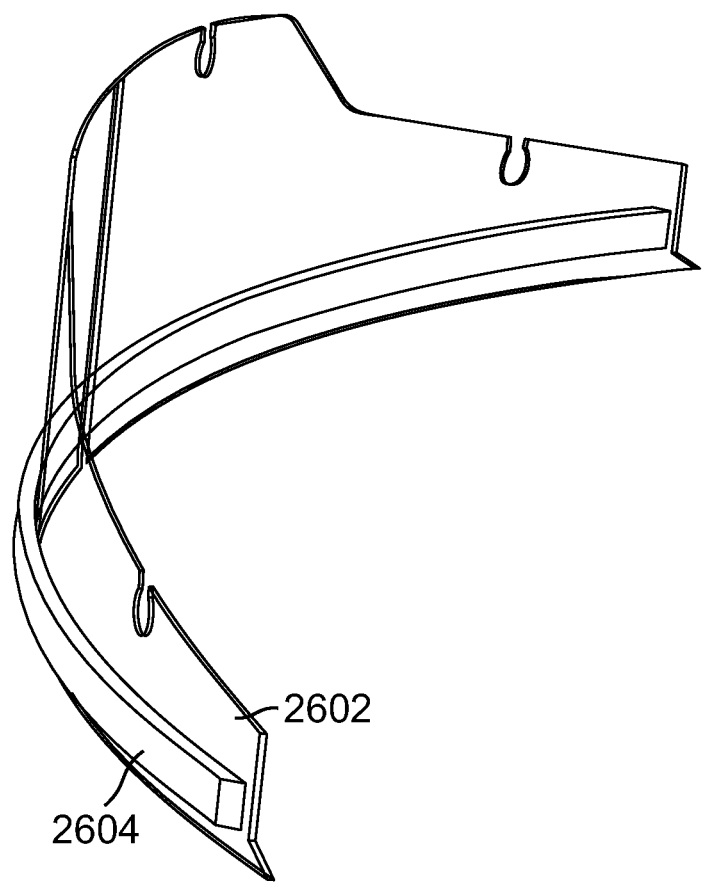
FIG. 28 shows a perspective view of the inner layer of the double-layer mud visor of FIG. 27 with a layer spacer, in accordance with an embodiment.

FIG. 28 shows a perspective view of the inner layer of the double-layer mud visor of FIG. 27 with a layer spacer, in accordance with an embodiment. Spacer 2604 may be provided on a front surface of inner layer 2602. Spacer 2604 may be formed by elastic foam type material. Spacer 2604 may act as a hood for guiding and covering a top side 206*a* of roll-off film 206. In some embodiments, spacer 2604 is not provided in mud visor 2600 with inner layer 2602 acting as the film guide. Referring now to FIG. 26, a top portion of outer layer 2606 may be laminated or bonded to inner layer 2602 with a lower portion of outer layer 2606 hanging or resting freely on spacer 2604 or directly on inner layer 2602 if spacer 2604 is not provided. As such, a top portion 206*a* of roll-off film 206 may travel through a gap 2610 formed between inner layer 2602 and outer layer 2606 when being conveyed across goggle lens 108.

Figure 29:
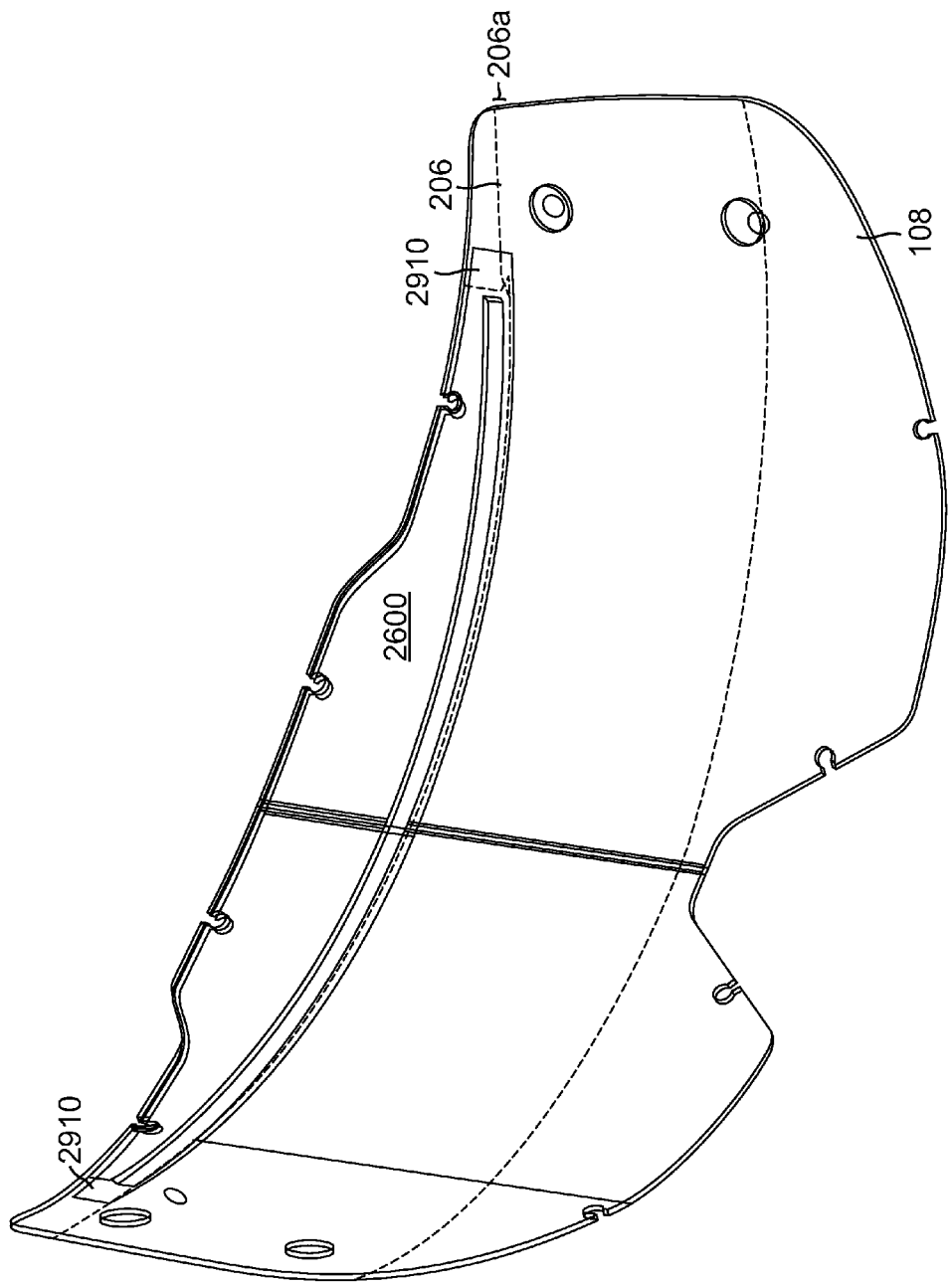
FIG. 29 shows a perspective view of the double-layer mud visor of FIG. 26 attached to a goggle lens, in accordance with an embodiment.

FIG. 29 shows a perspective view of the double-layer mud visor of FIG. 26 attached to a goggle lens, in accordance an embodiment. Inner layer 2602 may be attached to lens 108 by adhesives or adhesive tapes in a similar manner as that of mud visor 1800. As shown in FIG. 26, outer layer 2606 may extend further horizontally than inner layer 2602. As such, side end portions 2910 of outer layer 2606 may be inserted under film dispensing and receiving canisters 202 and 204, respectively. As shown in FIG. 29, a top perimeter portion 206*a* of the roll-off film 206 (as shown in dashed line) may be inserted between the inner layer 2602 and the outer layer 2602 below the spacer 2604.

Figure 30:
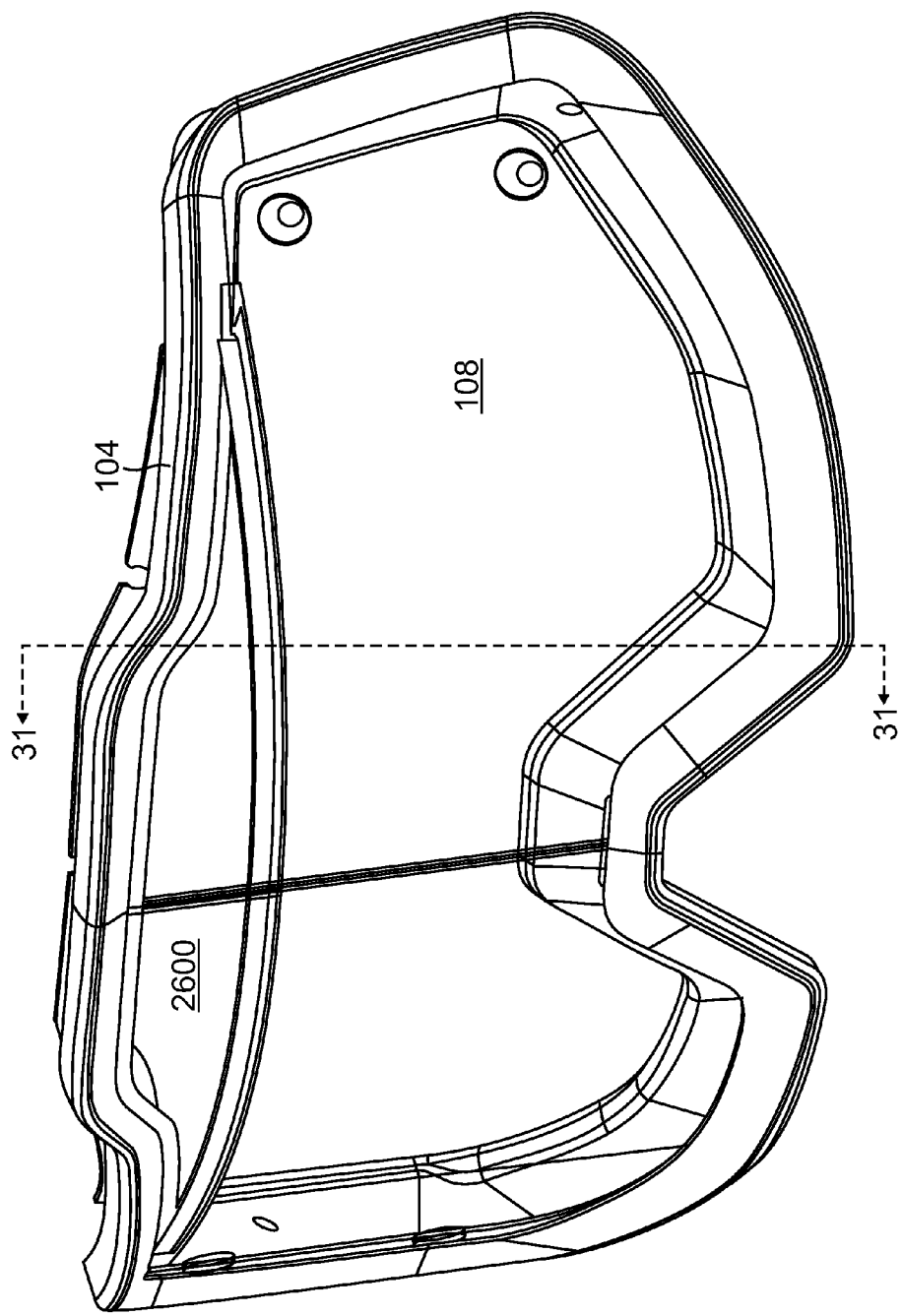
FIG. 30 shows a perspective view of the double-layer mud visor of FIG. 26 attached to the goggle lens and to an adaptor, in accordance with an embodiment.
Figure 31:
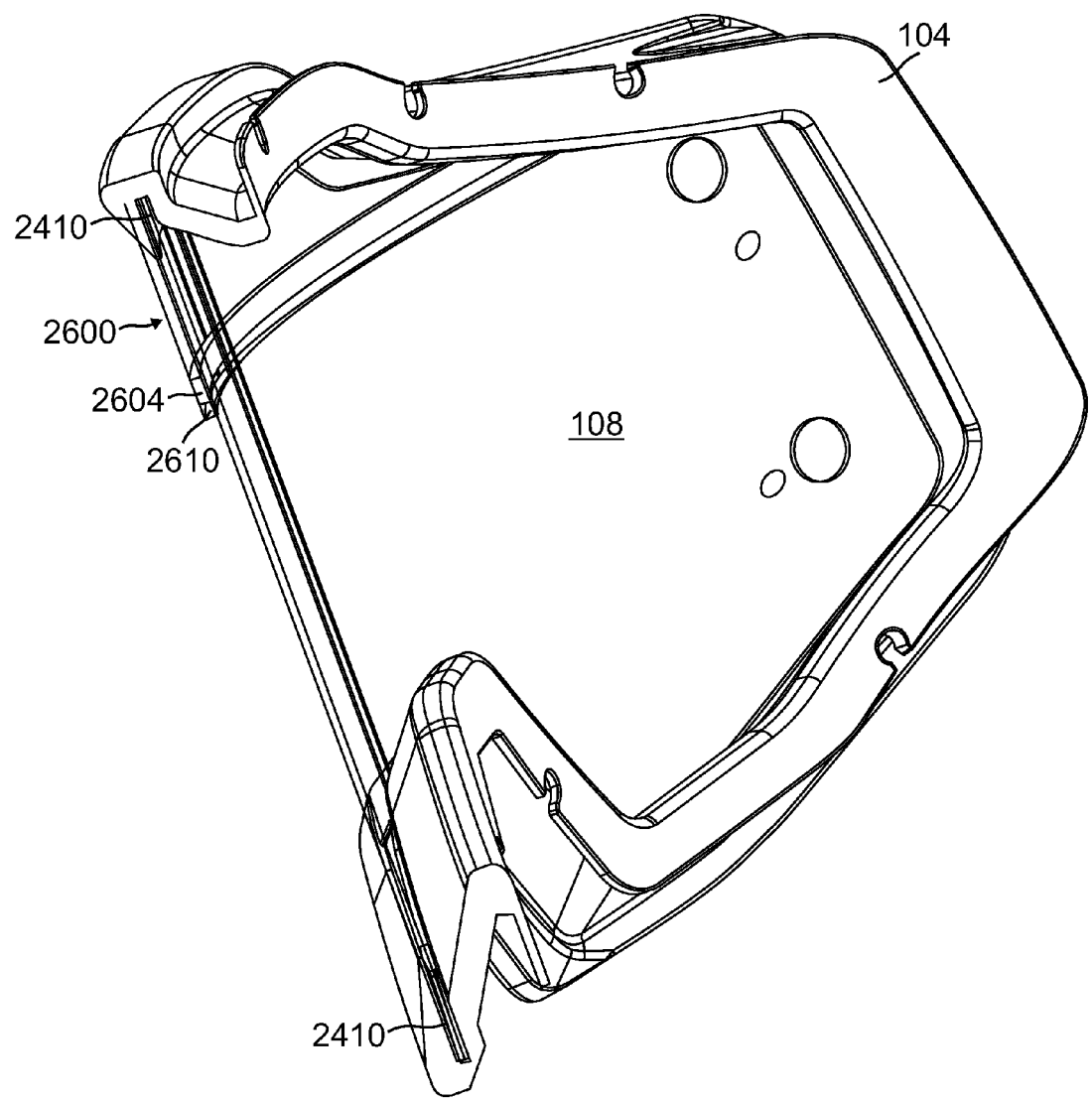
FIG. 31 shows a cross sectional view of the double-layer mud visor, goggle lens, and adaptor assembly taken along line 31-31 of FIG. 30, in accordance with an embodiment.

FIG. 30 shows a perspective view of the mud visor of FIG. 26 attached to the goggle lens and to an adaptor, in accordance an embodiment. Lens 108 attached with mud visor 2600 may be inserted into a lens groove 2410 of adaptor 104, because mud visor 2600 is formed by substantially thin plastic films or plastic sheets. Adaptor 104 may then be attached to a goggle frame 106. In some embodiments, lens 108 attached with mud visor 2600 may be attached directly to a lens groove of goggle frame 106 without adaptor 104. FIG. 31 shows a cross sectional view taken along 31-31 of the mud visor 2600 attached to the goggle lens and the adaptor of FIG. 30, in accordance with an embodiment. As shown in FIG. 31, a top portion of lens 108 and a top portion of double-layer mud visor 2600 are both inserted into the lens groove 2410 of adaptor 104. In a case where adaptor 104 is not used, both the top portion of lens 108 and the top portion of double-layer mud visor 2600 may be inserted into the lens groove 2410 of goggle frame 106. Because mud visor 2600 is inserted into the lens groove 2410, mud or liquid may be prevented from entering between mud visor 2600 and lens 108 from the top side. In some embodiments, both the top portion of inner layer 2602 and the top portion of outer layer 2606 are inserted into the lens groove 2410. In other embodiments, a shorter inner layer 2602 may be provided such that only the top portion of outer layer 2606 is inserted into the lens groove 2410.

Figure 32:
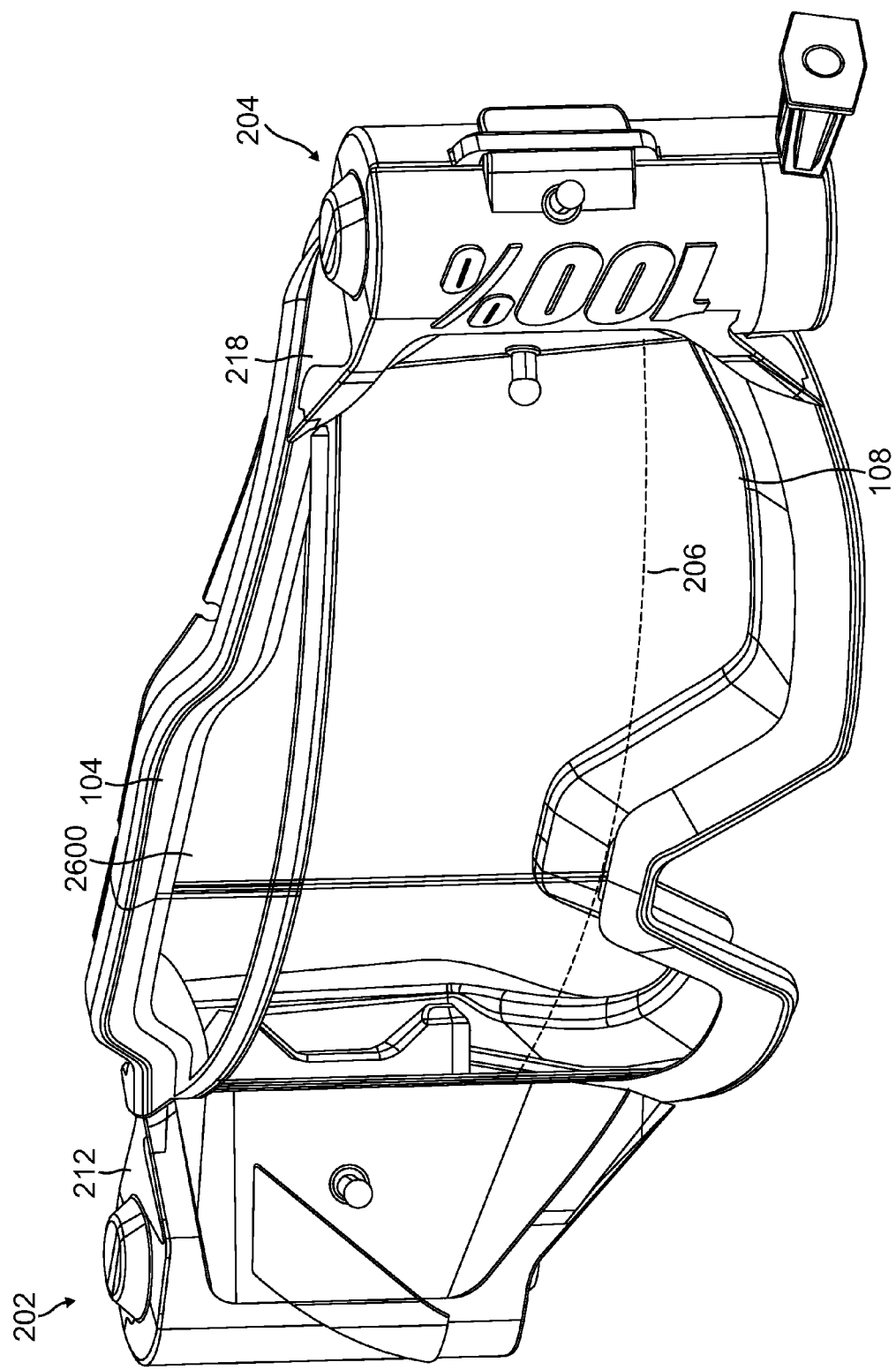
FIG. 32 shows a perspective view of a double-layer mud visor and a roll-off film system attached to a lens and an adaptor, in accordance with an embodiment.

FIG. 32 shows a perspective view of a double-layer mud visor and a roll-off film system attached to a lens and an adaptor, in accordance with an embodiment. Double-layer mud visor 2600 may extend horizontally across lens 108 to reach both film dispensing canister 202 and film receiving canister 204. In particular, as shown in FIG. 32, upper wing portion 218 of film receiving canister 204 may cover an end portion 2910 of mud visor 2600. Similarly, upper wing portion 212 of film dispending canister 202 may cover the other end portion 2910 of double-layer mud visor 2600. In particular, both end portions 2910 of outer layer 2606 may fit under the respective upper wing portions 212 and 218 of film dispending canister 202 and film receiving canister 204. This may allow seamless coverage of mud visor 2600 from the film dispending canister 202 to film receiving canister 204.

According to the above described embodiments, by forming mud visors 1800/2600 using a clear or transparent plastic film or sheet, the user's field of view on the goggle lens may be improved. Inserting mud visor 1800/2600 along with the goggle lens into the goggle frame or goggle adaptor may prevent mud or debris from entering behind the mud visor 1800/2600 from the top side. In addition, the horizontal ends of the mud visor also may be fitted under the film canisters 202 and 204 to provide seamless coverage to prevent mud from entering between the film canisters 202 and 204 and the mud visor.

In contrast, conventional mud visors may include a layer of plastic film attached to a lens via a layer of opaque spacer foam which may reduce the field of view of the user. Further, the spacer foam may not be attached to the lens properly and the bubbles or creases formed in the spacer foam may allow mud to enter behind the film. Also, because the spacer foam does not stretch entirely across the lens, openings may formed beyond the stretch of spacer foam between the film and the lens that may allow mud to enter. Thus, improvements as described in the above embodiments may mitigate one or more of these problems of the conventional mud visors.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected is:

1. An apparatus comprising:
   a substantially transparent goggle lens; and
   a substantially transparent mud visor removably attached to the goggle lens and extending across and covering a top portion of a viewable area of the goggle lens as used by a user when worn, wherein the mud visor comprises:
      a lens contacting portion provided on the goggle lens and disposed to directly cover the top portion of the viewable area of the goggle lens, and
      a film covering portion coupled to or adjacent to the lens contacting portion and disposed to cover and directly contact a top portion of a roll-off film conveyed across the goggle lens, such that the top portion of the roll-off film is disposed between the film covering portion and the goggle lens.

2. The apparatus of claim 1, wherein the mud visor comprises a substantially transparent plastic sheet.

3. The apparatus of claim 1, wherein the film covering portion of the mud visor further comprises:
   an overhang portion protruding away from a front surface of the goggle lens; and
   a film contacting portion extending from the overhang portion toward the front surface of the goggle lens and configured to press the top portion of the roll-off film toward the front surface of the goggle lens.

4. The apparatus of claim 1, wherein the film covering portion is configured to guide the roll-off film as the roll-off film is conveyed across the goggle lens.

5. The apparatus of claim 1, further comprising a goggle frame comprising a lens groove configured to receive the goggle lens, wherein the mud visor further comprises an upper portion configured to insert, along with the goggle lens, into the lens groove.

6. The apparatus of claim 5, wherein the goggle frame is an adaptor attachable to another goggle frame.

7. The apparatus of claim 5, wherein the upper portion comprises a partially circular cutout configured to insert into the lens groove to attach the mud visor to the goggle frame.

8. The apparatus of claim 1, further comprising:
   the roll-off film;
   a film dispensing canister configured to store and dispense the roll-off film; and
   a film receiving canister configured to receive the roll-off film dispensed from the film dispensing canister, wherein the film dispensing canister and the film receiving canister cover side ends of the film covering portion of the mud visor, respectively, and wherein the side ends of the film covering portion of the mud visor transition from an overhang shape to a substantially flat shape.

9. The apparatus of claim 1, wherein the lens contacting portion comprises a visor curvature parallel with a lens curvature of the goggle lens.

10. The apparatus of claim 1, wherein the mud visor is attached to the goggle lens by a substantially transparent material applied to a perimeter area of the lens contacting portion of the mud visor.

11. The apparatus of claim 1, wherein the mud visor further comprises:
    an inner layer contacting the goggle lens; and
    an outer layer covering the inner layer, wherein the top portion of the roll-off film is conveyed to slide between the inner layer and the outer layer, wherein the mud visor further comprises a spacer disposed between the inner layer and the outer layer, the spacer comprising an elastic foam material configured to guide the roll-off film conveyed across the goggle lens, and wherein the top portion of the roll-off film is guided between the inner layer and the outer layer and below the spacer while the roll-off film is conveyed across the goggle lens.

12. The apparatus of claim 1, wherein the top portion of the viewable area extends from a top edge of the goggle lens to the top of the roll-off film, wherein the lens contacting portion comprises a visor curvature parallel with a lens curvature of the top portion of the viewable area, and wherein the substantially transparent mud visor extends across and covers substantially all of the top portion of the viewable area such that a viewer looking through the top portion of the viewable area would also look through the substantially transparent mud visor.

13. The apparatus of claim 1, wherein the lens contacting portion extends downward substantially parallel with the top portion of the viewable area of the goggle lens.

14. A method of attaching a mud visor to a goggle system, the method comprising:
providing a substantially transparent goggle lens;
removably attaching a substantially transparent mud visor to the goggle lens, wherein the mud visor extends across and covers a top portion of a viewable area of the goggle lens, the mud visor comprising:
a lens contacting portion provided on the goggle lens and disposed to directly cover the top portion of the viewable area of the goggle lens, and
a film covering portion coupled to the lens contacting portion, the film covering portion covering and directly contacting a top portion of a roll-off film conveyed across the goggle lens, such that the top portion of the roll-off film is disposed between the film covering portion and the goggle lens.

15. The method of claim 14, further comprising:
applying adhesive material along a perimeter portion of the lens contacting portion of the mud visor,
aligning a top perimeter edge of the mud visor with a top perimeter edge of the goggle lens,
adhering the lens contacting portion of the mud visor to the top portion of the goggle lens; and
inserting the goggle lens along with an upper portion of the mud visor into a lens groove of a goggle frame.

16. The method of claim 15, further comprising attaching the goggle frame to another goggle frame.

17. The method of claim 14, further comprising:
attaching a roll-off film system to the goggle lens, wherein the roll-off film system comprises:
the roll-off film,
a film dispensing canister configured to store and dispense the roll-off film, and
a film receiving canister configured to receive the roll-off film dispensed from the film dispensing canister;
covering respective end portions of the mud visor with the film dispensing canister and the film receiving canister;
stretching the roll-off film dispensed between the film dispensing canister and the film receiving canister across the goggle lens;
inserting a top portion of the roll-off film under a lower portion of the mud visor;
conveying the roll-off film across the goggle lens from a film dispensing canister to a film receiving canister; and
guiding the top portion of the roll-off film along the mud visor as the roll-off film is conveyed across the goggle lens.

18. The method of claim 14, wherein the lens contacting portion comprises a visor curvature parallel with a lens curvature of the goggle lens.

19. The method of claim 14, wherein the top portion of the viewable area extends from a top edge of the goggle lens to the top of the roll-off film, wherein the lens contacting portion comprises a visor curvature parallel with a lens curvature of the top portion of the viewable area, and wherein the substantially transparent mud visor extends across and covers substantially all of the top portion of the viewable area such that a viewer looking through the top portion of the viewable area would also look through the substantially transparent mud visor.

20. The method of claim 14, wherein the lens contacting portion extends downward substantially parallel with the top portion of the viewable area of the goggle lens.

* * * * *